United States Patent
Nie et al.

(10) Patent No.: US 10,487,312 B2
(45) Date of Patent: Nov. 26, 2019

(54) PASSAGING AND HARVESTING FORMULATION AND METHOD FOR HUMAN PLURIPOTENT STEM CELLS

(71) Applicant: LONZA WALKERSVILLE INC., Walkersville, MD (US)

(72) Inventors: Ying Nie, Frederick, MD (US); Jonathan Allen Rowley, Walkersville, MD (US); Thomas Fellner, Frederick, MD (US); Patrick Walsh, Gaithersburg, MD (US)

(73) Assignee: LONZA WALKERSVILLE INC., Walkersville, MD (US)

( * ) Notice: Subject to any disclaimer, the term of this patent is extended or adjusted under 35 U.S.C. 154(b) by 0 days.

(21) Appl. No.: 15/843,078

(22) Filed: Dec. 15, 2017

(65) Prior Publication Data
US 2018/0171300 A1    Jun. 21, 2018

Related U.S. Application Data

(62) Division of application No. 14/117,687, filed as application No. PCT/US2012/038321 on May 17, 2012, now Pat. No. 9,885,019.

(60) Provisional application No. 61/487,087, filed on May 17, 2011.

(51) Int. Cl.
*C12N 5/0775* (2010.01)
*C12N 5/0735* (2010.01)
*C12N 5/074* (2010.01)

(52) U.S. Cl.
CPC ......... *C12N 5/0662* (2013.01); *C12N 5/0606* (2013.01); *C12N 5/0607* (2013.01); *C12N 5/0663* (2013.01); *C12N 2500/14* (2013.01)

(58) Field of Classification Search
None
See application file for complete search history.

(56) References Cited

U.S. PATENT DOCUMENTS

| | | | |
|---|---|---|---|
| 5,276,145 A | 1/1994 | Bottenstein | |
| 5,968,753 A | 10/1999 | Tseng-Law et al. | |
| 6,458,781 B1 | 10/2002 | Connor et al. | |
| 2009/0311765 A1 | 12/2009 | Maguire et al. | |
| 2010/0098725 A1* | 4/2010 | Liu | A61K 39/145 424/209.1 |
| 2011/0111030 A1 | 5/2011 | Bhasin | |

FOREIGN PATENT DOCUMENTS

| | | |
|---|---|---|
| JP | H09508534 A | 9/1997 |
| WO | 1995034817 A1 | 12/1995 |
| WO | 2010035136 A2 | 4/2010 |

OTHER PUBLICATIONS

Joannides et al, Stem Cells, 24:230-235 (2006) (Year: 2006).*
Saura et al., GLIA, 44:183-189 (2003) (Year: 2003).*
Thomas et al., Cytotechnol., 55:31-39 (2007) (Year: 2007).*
Cohen, Jonah, et al.: "Survival of porcine mesenchymal stem cells over the alginate recovered cellular method." Journal of Biomedical Materials Research, vol. 96A, No. 1, Jan. 2011, pp. 93-99, XP002678837.
Bai, Yunling, et al.: "Role of Iron and Sodium Citrate in Animal Protein-Free CHO Cell Culture Medium on Cell Growth and Monoclonal Antibody Production," Biotechnology Progress, vol. 27, No. 1, Jan. 2011, pp. 209-219, XP002678838.
Ellerstrom, Catharina, et al.: "Facilitated Expansion of Human Embryonic Stem Cells by Single-Cell Enzymatic Dissociation," Stem Cells (Miamisburg), vol. 25, No. 7, Jul. 2007, pp. 1690-1696, XP002678839.
Thomson, Alison, et al.: "Human Embryonic Stem Cells Passaged Using Enzymatic Methods Retain a Normal Karyotype and Express CD30." Cloning and Stem Cells. vol. 10, No. 1, Mar. 2008. pp. 89-106, XP002678840.
De Smedt, Ann, et al.: "Optimisation of the cell cultivation methods in the embryonic stem cell test results in an increased differentiation potential of the cells into strong beating myocard cells." Toxicology in vitro, Elsevier Science, GS, vol. 22, No. 7, Oct. 1, 2008, pp. 1789-1796, XP025431116.
T'Joen, V., et al..: "Expansion of human embryonic stem cells, a comparative study." Cell Proliferation. vol. 44, No. 5, Oct. 2011, pp. 462-476, XP002678841.
Müller, Thomas, et al.; "A novel embryonic stem cell line derived from the common marmoset monkey (Callithrix jacchus) exhibiting germ cell-like characteristics;" vol. 24, No. 6, 2009, pp. 1359-1372.
Dulbecco, R., et al.; "Plaque Formation and Isolation Of Pure Lines With Poliomyelitis Viruses", J. Exp. Med. 1954, 99, pp. 167-182.
Wikipeida, Phosphate-buffered saiine, https://en.wikipedia.org/wiki/Phosphate-buffered_saline (last visited Nov. 17, 2016).
ThermoFisher Scientific, Technical Resources, 20012—PBS, pH 7.2, http://www.thermofisher.com/us/en/home/technical-resources/media-formulation.158.html (last visited Nov. 17, 2016).

(Continued)

*Primary Examiner* — Thomas J. Visone
(74) *Attorney, Agent, or Firm* — Gianna J. Arnold; Saul Ewing Arnstein & Lehr LLP

(57) ABSTRACT

Formulations and methods are disclosed for the harvesting and subsequent passaging of human pluripotent stem cells without the use of enzymes and/or scraping to dislodge cells from cell culture vessels. The formulations and methods permit the harvesting of cells as large clusters from the surface of various cell culture vessels including multilayer cell culture vessels. Further, the formulations and methods provide high yields of harvested cells for subsequent passaging and high post-harvest cell viability. Pluripotent stem cells passaged with the formulations according to the methods remain undifferentiated and express typical stem cell markers, while, at the same time, they retain the differentiation capability and are able to differentiate into the cells in all three germ layers and generate teratomas, even after numerous rounds of harvesting and passaging. These hPSCs also maintain normal karyotype after passaged with the formulations for extended period of time.

9 Claims, 47 Drawing Sheets

(56) References Cited

OTHER PUBLICATIONS

Cold Spring Harbor Protocols, Phosphate-buffered saline (PBS) (1999).
Nicklin, Methods in Molecular Medicine, Humana Press Inc., Chapter 22 (1999).
Stanley, <http://stanxterm.aecom.yu.edu/wiki/index.php?page=Removing cells without trypsinization> Accessed Aug. 25, 2016 (2005).
Gray, et al., J. Nucl. Med., 13:147-150 (1977).
Molosh, et al., Neuropsychopharmacology, 35:1333-1347 (2010).
Cold Spring Harbor Protocols (2009).
Li, et al., Human Repro., 24(3):580-589 (2009).
Al-Ayoubl, et al., J. Cell. Biochem., 105:875-884 (2008).
Kim, AFCS Solution Protocol (2002).
Perka, et al., Tiss. Eng., 7(3):359-361 (2001).
Xu, et al., Osteoarthritis and Cartilage. 18:433-439 (2010).

* cited by examiner

Scraping inflicts damage to the cells. Without scraping, post-detachment viability of hESCs nearly doubled.

Sodium citrate disrupts cell-surface bond more than EDTA/EGTA. hESC colonies treated with sodium citrate do not re-stick onto the culturing surface after 1 min incubation IN MEF-CM

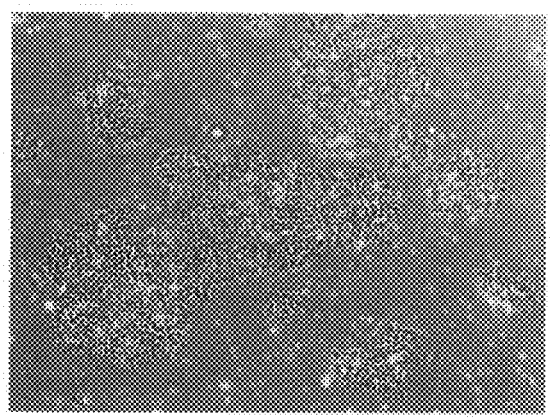
Day 1
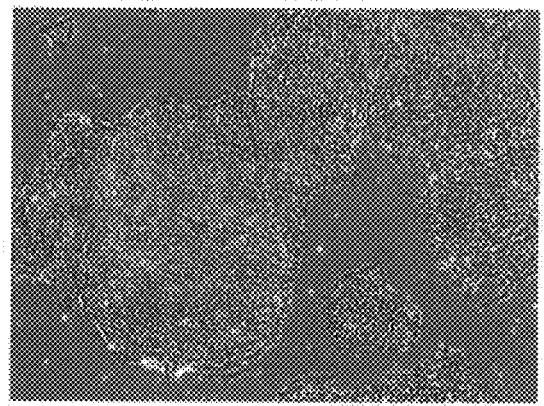
Day 2
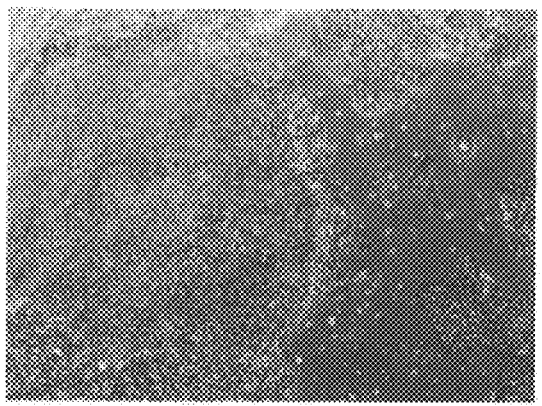
Day 3
FIGURE 3

**EDTA Harvest Remainder
45% detached**

**EDTA Harvest Remainder
70% detached**

A and B showing operator variances

**SC-Harvest Remainder
90% detached**

Prolonged sodium citrate treatment (shown here as 11 min treatment) does not break hESC colonies grown in MEF-CM into detached single cells. Instead, the size of the detached clumps is dependent of sodium citrate dosage : the higher the dosage, the bigger the clumps.

Formulations

|  | Solution 1 | Solution 2 | Solution 3 | Solution 4 | Solution 5 | Solution 6 |
|---|---|---|---|---|---|---|
| Osmo (Predic) | 133 | 265 | 400 | 530 | 795 | 1060 |
| Osmo (Actual) | 169 | 299 | 418 | 548 | 781 | 1016 |
| SC mM (final) | 15 | 15 | 15 | 15 | 15 | 15 |
| KCl mM (final) | 68 | 135 | 203 | 270 | 405 | 540 |

- Constant SC concentration (15 mM)
- A series of osmo achieved by adjusting KCl concentration

FIGURE 13

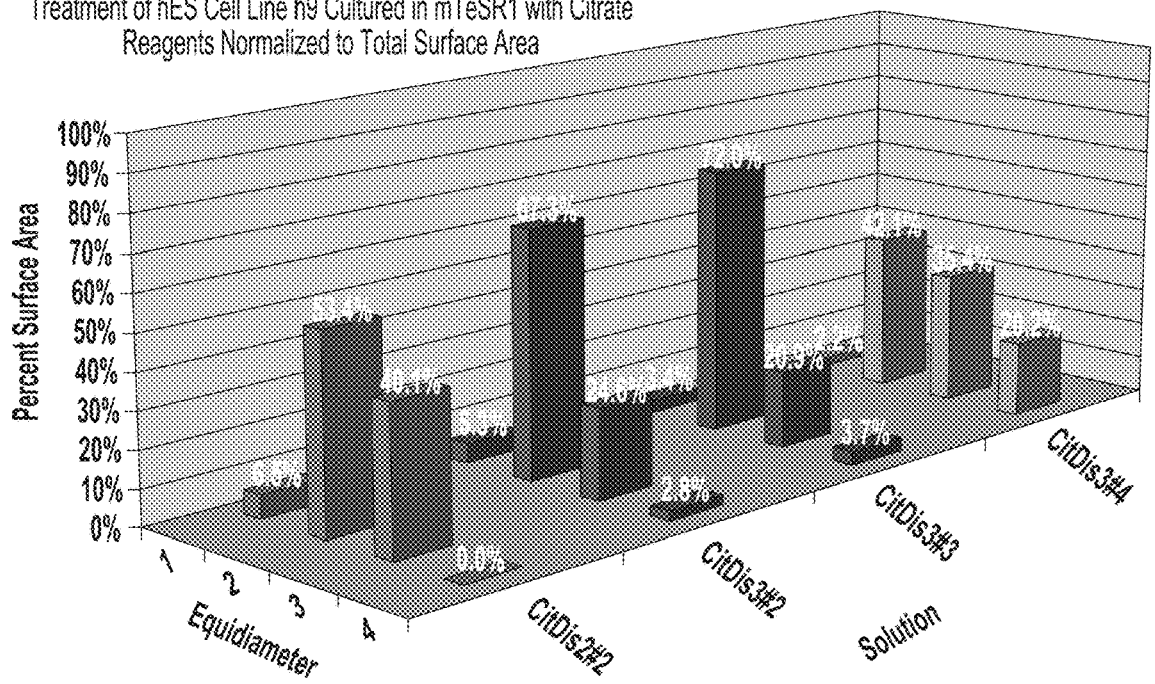
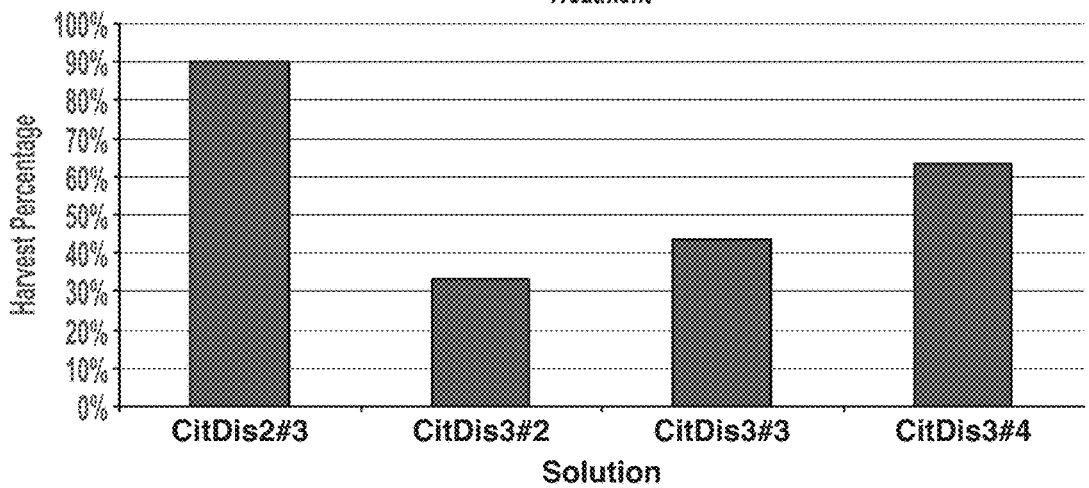
| | | formulations | | | |
|---|---|---|---|---|---|
| | Versene (EDTA) | Dis2Sol3 (best at 5min) | Dis3Sol2 | Dis3Sol3 | Dis3Sol4 |
| Citrate (mM) | | 15 | 7.5 | 15 | 30 |
| KCl (mM) | | 203 | * | * | * |
| NaHPO4 | (control) | | * | * | * |
| mOsmo | | 418 | 265 | 265 | 265 |
| pH | | 7.9 | 7.2 | 7.2 | 7.2 |
FIGURE 17

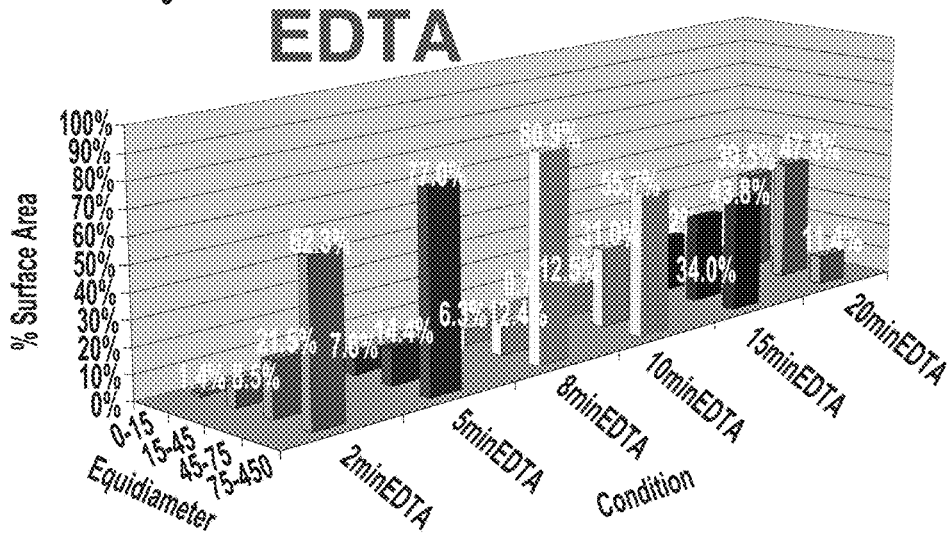
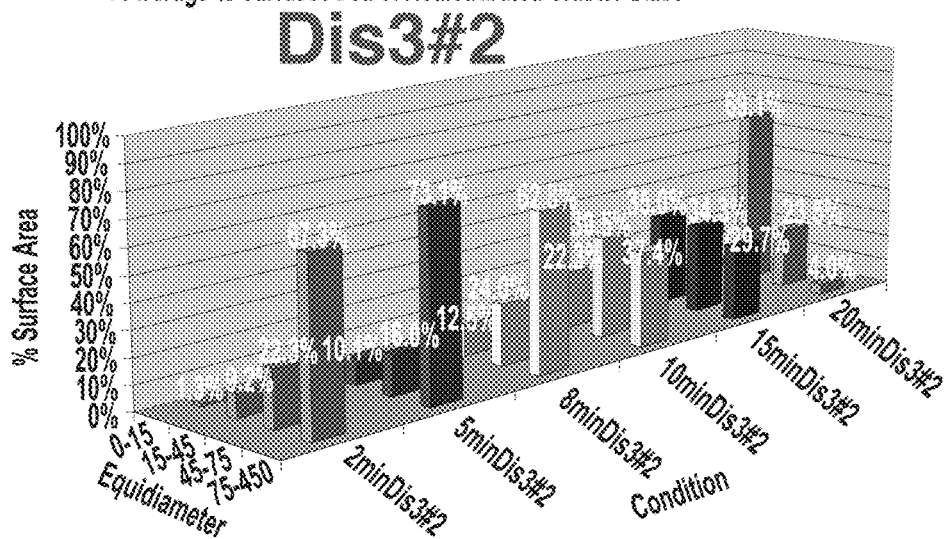
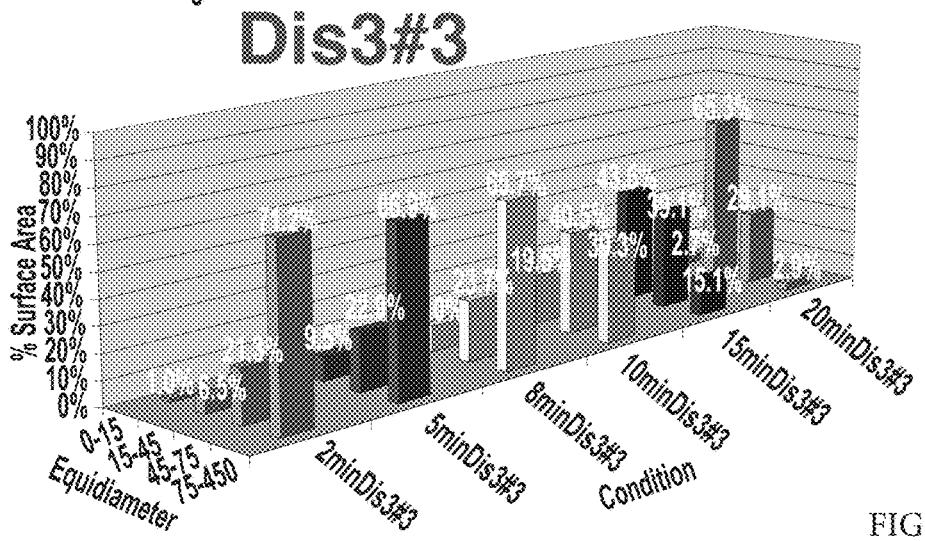
FIGURE 18B-1

Selected Formulations

|  | [citrate] | [KCl] | mOsmo | Performance | Application |
|---|---|---|---|---|---|
| #3 | 10mM | 300mM | 570 | 85-90% harvest between 5-20min, >70% P.E. at 10min treatment | both small scale (5min) and large scale (10min) |
| #13 | 1mM | 316mM | 570 | 50% at 5min and 90% harvest at 10min treatment, >50% P.E. at 10min treatment | large scale and downstream process (big and robust clusters) |
| Dis2#3 | 15mM | 203mM | 418 | 90% harvest at 5min treatment, 65% P.E. at 5min and 40% P.E. at 10min treatment | small scale (fast treatment) and dry passage |

FIGURE 23

- Citrate formulations optimized for hESC detachment can be used for MSC detachment and passage
- Solution #3 performs the best for MSCs
  - 10min Citrate3 treatment followed by tapping is sufficient to detach 80% cells, with 90% post-detachment viability Immunocytochemistry of long term hESC cultures: hESCs passaged with citrate solution #13 for 31 passages in StemPro, and 34 passages in mTeSR1, respectively, stained positive for pluripotency markers, including OCT4, Sox2, Nanog, SSEA4, Tra-1-60 and Tra-1-81.

Immunocytochemistry of embryoid body differentiation of hESCs: hESCs passaged with citrate solution #13 for 40 passages in StemPro, and 35 passages in mTeSR1, respectively, were capable of differentiating into all three germ layers, shown by the positive staining of the markers for the germ layers (AFP for endoderm, SMA for mesoderm and Tuj for ectoderm).

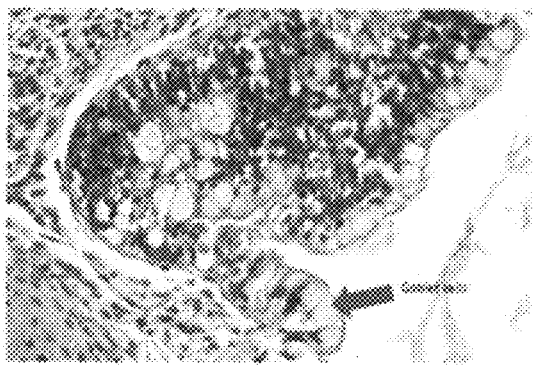
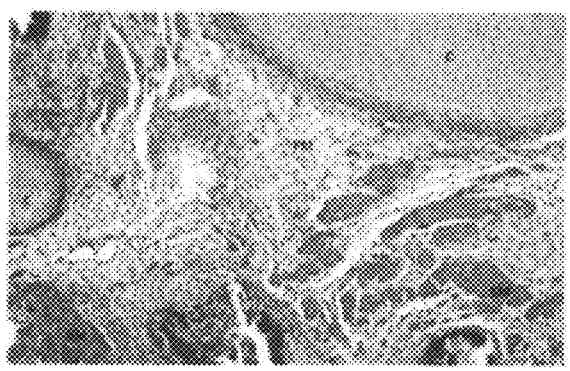
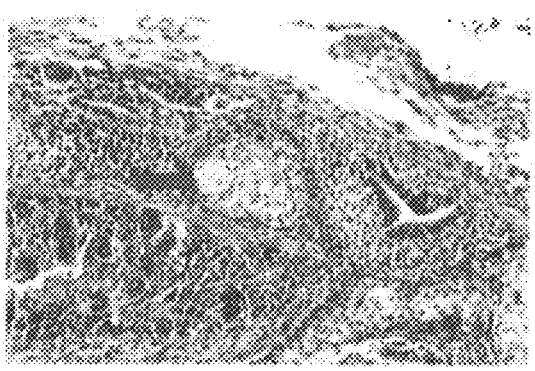
Histology of teratomas: hESCs passaged with citrate solution #13 for 28 passages in StemPro were capable of generating teratomas when injected into immunodifficient mice.
FIGURE 31

PASSAGING AND HARVESTING FORMULATION AND METHOD FOR HUMAN PLURIPOTENT STEM CELLS

CROSS-REFERENCE TO RELATED APPLICATIONS

The invention is a divisional and claims priority to U.S. application Ser. No. 14/117,687, filed on Feb. 28, 2014, which is a national phase of PCT/US2012/038321, filed on May 17, 2012, which claims the benefit of priority to U.S. Provisional Patent Application No. 61/487,087, filed on May 17, 2011, the entire contents of each of which are hereby incorporated in total by reference.

FIELD OF THE INVENTION

The present invention relates to a formulation and method for harvesting/passaging pluripotent stem cells. Specifically, the present invention relates to 1/ formulations including sodium citrate and a method of use thereof; 2/ methods of identifying formulations based on the $Ca^{2+}$ chelator concentration and osmolarity; and 3/ use of such formulations.

BACKGROUND OF THE INVENTION

Human pluripotent stem cells (hPSCs), including human embryonic stem cells (hESCs) and induced pluripotent stem cells (iPSCs), can proliferate indefinitely in culture while maintaining the capability to differentiate into multiple types of somatic cells. These cells are greatly valued as providing unlimited cell source in cell therapy and regenerative medicine. As demonstrated by recent FDA approval of clinical trials, human embryonic stem cell (hESC)-based cell therapies are progressing from bench to clinic. However, currently available plate and T-flask-based culture platforms severely limit the scalability of hPSCs production to commercially relevant lot sizes. To unleash the potential of hPSCs in cell therapy and regenerative medicine, a scalable hPSC manufacturing process must be developed. Scaling up existing flask-based processes is a critical stepping stone in translating current hPSC research into clinical application. One of the biggest challenges is to establish a scalable passaging method for large scale multilayer vessels that maintains high yield, pluripotent phenotype, and karyotypic stability.

Traditionally, hPSCs are harvested and passaged as colony fragments by mechanical scraping with or without pre-treatment with enzymes (such as collagenase or Dispase®). This process is labor intensive and cannot be applied in culturing hPSCs in multilayer cell culture vessels, the platform widely used in producing commercial scale adherent cells. Cells growing in multilayer cell culturing vessels cannot be accessed for scraping. In addition, mechanical scraping causes damage to cells. Without scraping, cell viability can increase up to 90 percent. Known methods related to single-cell passaging and harvesting are not desirable due for example, to concerns related to low post-passaging and cryopreservation recovery and abnormal karyotype, associated with low cloning efficiency of hPSCs. Although Rho-associated kinase inhibitors (ROCK Inhibitors) have been reported to be able to improve hPSC cloning efficiency, the mechanism is not fully understood and the effect of ROCK Inhibitors on hPSC culture is yet to be evaluated. Therefore, passaging hPSCs as single cells in the presence of ROCK Inhibitors is not widely accepted.

Recently, passaging hESCs with non-enzymatic cell detachment solutions, mainly EDTA (ethylene diamine tetraacetic acid) solutions, has been adopted by some hESC labs and is spreading from academic labs into industry. One of the commercially available EDTA-containing solutions for cell dissociation is Versene® EDTA, which contains 0.55 mM EDTA and has been used for harvesting and passaging hPSCs. The typical procedure of passaging hESCs with Versene® EDTA starts with washing the culture with $Ca^{2+}$/$Mg^{2+}$-free buffer (for example, Dulbecco's phosphate-buffered saline; DPBS), followed by incubating the culture in Versene® EDTA for 4-9 minutes. Versene® EDTA is then removed and cells are physically removed from the surface as clusters by manual hosing of the cells with culture medium via pipetting. Compared with the conventional enzymatic-treatment-followed-by-scraping method (see Table 1), the advantage of this method is that (1) it uses a non-enzymatic solution—thus, there is no need for post-detachment washing or centrifugation to eliminate enzyme, and (2) it does not require scraping—the cells treated with Versene® EDTA can be washed off the surface. As described in Table 1, and illustrated in FIG. 1, compared with hESCs treated with enzyme and scraped off the culturing surface, the hESCs treated with Versene® EDTA and detached without scraping have higher post-detachment viability and re-attach to the new culturing surface much faster (minutes vs. hours) when passaged.

TABLE 1

Methods of Harvesting/Passaging hESCs

| Conventional Enzymatic and Scraping Method | Versene ® EDTA Method |
| --- | --- |
| 1. remove culture medium | 1. remove culture medium |
| 2. incubate in collagenase or Dispase ® at 37° C. for 2-5 minutes | 2. wash once with $Ca^{2+}$/$Mg^{2+}$-free buffer (for example, DPBS) |
| 3. remove collagenase or Dispase ® | 3. incubate in Versene ® EDTA at room temperature for 4-9 minutes |
| 4. wash three times with culture medium | 4. remove Versene ® EDTA |
| 5. scrape hESCs off the surface in culture medium with cell scraper or pipette tip | 5. hose the cells off the surface with culture medium |
| 6. collect the colony clumps (harvest) or transfer into a fresh culture vessel (passage) | 6. collect the cell clusters (harvest) or transfer into fresh culture vessel (passage) |

However, when applied into expanding hESC in multilayer vessels, the Versene® EDTA passaging/harvesting method is not ideal. Versene® EDTA seems to breaks down cell-cell association faster than it breaks cell-surface bonding. If hESC culture is over-treated with Versene® EDTA (>9 minutes), a greater percentage of cells come off the surface as single cells rather than clusters or clumps. In order to avoid getting too many single cells, the treatment time normally is controlled between seven to nine minutes. After the removal of Versene® EDTA, in six-well plate or T-flask culture format, fluidic shear force generated by hosing with culture medium via manual pipetting is needed to dislodge the cells off the surface. However, hESC culture in multilayer vessels cannot be manually sheared with culture medium as pipettes cannot be introduced inside the vessels. Instead, in this culture format, after Versene® EDTA is replaced with culture medium, vigorous tapping is applied to dislodge the cells. The mechanical force (tapping) has to follow the replacement of Versene® EDTA with culture medium immediately because Versene® EDTA treated hESCs quickly re-attach to the surface once they come in contact with culture medium. In fact, with the current state-of-art, it is only possible to harvest 40-70% of the entire culture in multilayer cell factories—dramatically impacting the yield of these very expensive cells. One possible solution to increase the yield is not to replace Versene® EDTA with culture medium and to dislodge the cells in Versene® EDTA instead. However, in this case, the exposure time of cells to Versene® EDTA is increased, which increases the risk of getting too many single cells and obtaining karyotypic unstable colonies. In addition, extra steps of post-detachment processing have to follow to remove or neutralize Versene® EDTA from the final harvest, which will not only add to the labor intensity but also further the breakup of the small hESC clusters.

There is therefore a need for a scalable and high-yielding passaging and harvesting formulation and method for hPSCs that eliminates or reduces the drawbacks of methods known in the art.

SUMMARY OF THE INVENTION

The present invention provides a non-enzymatic reagent formulation and a method of harvesting and subsequently passaging pluripotent stem cells as clusters with high yield and high post-detachment cell viability.

It is an object of the invention to provide a scalable and high-yielding passaging and harvesting formulation and method for hPSCs that eliminates or reduces the drawbacks of methods known in the art.

It is a further object of the invention to provide a formulation comprising sodium citrate.

It is a further object of the invention to provide a formulation and method optimized for harvesting and passaging hPSCs in reference to hPSC parameters such as high viability, high yield, large post-detachment cluster size, serial passageability, and maintenance of the pluripotent phenotype (for example, expression of markers typically associated with stem cells such as OCT4, Sox2, Nanog, SSEA4, TRA-1-60 and TRA-1-81) and karyotypic stability.

It is a further object of the invention to provide a formulation and method that can be used in any hPSC lab as routine lab practice to expand hPSC cultures with reduced labor intensity and process time.

It is a further object of the invention to provide a formulation and related method that does not require mechanical scraping to remove cells from the surface of the culture vessel.

It is a further object of the invention to provide a formulation and related method wherein the harvested cells do not need to be washed and centrifuged to remove the agents used to detach the cells from the surface of the culture vessel.

It is a further object of the invention to provide a formulation and method, whereby over 90% of hPSCs grown in multilayer cell culture vessels can be harvested with over 90% viability.

It is a further object of the invention to provide a closed and scalable hPSC manufacturing process through culturing hPSCs in multilayer cell culture vessels and by washing, concentrating, vialing and cryopreserving cell harvest with automatic downstream processing technology.

It is a further object of the invention to provide a process of expanding and passaging hPSCs from T-flasks into multilayer cell factories with a novel non-enzymatic harvesting and passaging method, followed by downstream processing with continuous counter-flow centrifugation technology (for example, kSep® technology).

It is a further object of the invention to provide a method of developing a cell-detaching solution for hPSCs wherein the size distribution of the detached clusters and the percentage of the culture detached at given treatment time can be controlled with the osmolarity and $Ca^{2+}$ chelator concentration.

It is a further object of the invention to provide a method for harvesting and subsequent passaging of hPSCs grown in suspension as aggregates or on microcarriers that includes incubating the hPSC aggregates or hPSCs on microcarriers, in either a formulation disclosed herein or a formulation identified by a method disclosed herein, in cell culture vessels for two to twenty minutes allowing the hPSC aggregates to disintegrate or to allow the hPSCs to detach from the microcarriers, with cell viability between about 85-100 percent.

It is a further object of the invention to provide a method for harvesting and subsequent passaging of hPSCs, where the hPSCs are passaged with a high split ratio (1:10 to up to 1:60; or density of cells at seeding of about $30E3/cm^2$ to as low as $5E3/cm^2$) and the culture reaches confluence within seven days after split.

It is a further object of the invention to provide a method for harvesting and subsequent passaging of hPSCs where the hPSCs maintain pluripotency and normal G-banding karyotype at over 50 passages.

It is a further object of the invention to provide formulations, and method of use thereof, providing for selectively detaching and passaging undifferentiated hPSCs.

It is a further object of the invention to provide a means for harvesting and subsequent cryopreserving hPSCs with high post thaw recovery and re-plating efficiency.

It is a further object of the invention to provide a method of downstream processing of harvested hPSC clusters in a closed system including continuous counter flow, centrifugation, formulation, automated vialing and cryopreservation with controlled rate freezer.

Accordingly, in one embodiment, a formulation is provided for harvesting and subsequent passaging of human pluripotent stem cells without scraping and without substantial loss of viability. In one aspect of the embodiment, the formulation includes, for example, sodium citrate, a salt, and a phosphate-buffered saline solution, at an osmolarity of about 250-1050 mOsmol/Liter. In an alternative aspect the osmolarity is 311-1014 mOsmol/Liter. In another aspect of the embodiment, the formulation is used to harvest and passage embryonic stem cells and induced pluripotent stem cells. The concentration of citrate is, for example, about 0.15 to 150 mMol/Liter. The salt is, for example, NaCl, KCl, $Na_2HPO_3$, $NaH_2PO_3$, $K_2HPO_3$, or $KH_2PO_3$. When the salt is KCl, the concentration is, for example, about 1.00-1400 mMol/Liter Alternatively, when the salt is KCl, the concentration is about 1.35-1350 mMol/Liter. In an aspect of the embodiment, the osmolarity of the formulation is, for example, about 400-700 mOsmol/Liter. In another aspect of the embodiment, the osmolarity of the formulation is, for example, about 418-570 mOsmol/Liter. In another aspect of the embodiment, the formulation is pH buffered with, for example, bicarbonate, phosphate, ethanolamine, triethanolamine, or trometamol. The pH of the formulation is, for example, about 7-8, In an alternative embodiment the pH is about 7.2-7.8. In one aspect the phosphate-buffered saline solution is, for example, $Ca^{2+}$/$Mg^{2+}$-free Dulbecco's phosphate buffered saline (DPBS). In some aspects of the embodiment, treatment of the cells with the formulation results in the harvest of, for example, at least 90% of the cells from the surface of the culture vessel and cell viability of, for example, at least 90%.

In another embodiment, a method is provided for producing a formulation for harvesting and subsequent passaging of human pluripotent stem cells without scraping and substantial loss of viability.

In another embodiment, a method is provided for harvesting and subsequent passaging of hPSCs comprising incubating the hPSCs in one of the formulations described in the preceding paragraphs and in cell culture vessels for a period of time to allow the hPSCs to detach from the cell culture vessels in clusters with high yield and high post-detachment cell viability of, for example, about 85-100%. In one aspect of the embodiment, the cell culture plates or vessels are, for example, petri dishes, multi-well cell culture plates, stacked cell culture apparatus, multilayer cell culture factories, and similar vessels known in the art to be capable of supporting the culture of hPSCs. In some aspects of the embodiment, the cells are treated with the formulation for about 2-20 minutes. In one embodiment, the treatment time is 5-15 min for hPSCs cultured in mTeSR1®. In another embodiment, the treatment time is 8-20 min for hPSCs cultured in StemPro®. (StemPro® and mTeSR1® are examples of commercially available defined media for hPSC culture.) In aspects of the embodiment, the cells are harvested in clusters with sizes ranging, for example, from about 10-1000 μm. More particularly, the cluster size is, for example, about 40-500 μm. In some aspects of the embodiment, the method results in the harvest of, for example, at least 90% of the cells from the surface of the culture vessel and cell viability of at least 90%.

In another embodiment additional passaging and harvesting formulations are provided including formulations containing EDTA and EGTA, other $Ca^{2+}$ chelators besides sodium citrate, or combinations of various $Ca^{2+}$ chelators. Two factors are identified related to cell detachment, the $Ca^{2+}$ chelator concentration and osmolarity.

In another embodiment, a method of developing a cell-detaching solution for hPSCs is provided wherein the size distribution of the detached clusters and the percentage of the culture detached at given treatment time can be controlled with the osmolarity and $Ca^{2+}$ chelator concentration.

These and other objects are achieved in the present invention.

There has thus been outlined, rather broadly, the more important features of the invention in order that the detailed description thereof that follows may be better understood, and in order that the present contribution to the art may be better appreciated. There are, of course, additional features of the invention that will be described further hereinafter.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that equivalent constructions insofar as they do not depart from the spirit and scope of the present invention, are included in the present invention.

For a better understanding of the invention, its operating advantages and the specific objects attained by its uses, reference should be had to the accompanying drawings and descriptive matter which illustrate preferred embodiments of the invention.

BRIEF DESCRIPTION OF THE DRAWINGS AND THE FIGURES

FIG. 1 illustrates the percent viability of hESCs detached from a culturing surface following enzymatic treatment and scraping vs. non-enzymatic treatment and non-scraping.

FIGS. 2A, 2B, and 2C illustrate EDTA/EGTA detachment vs. sodium citrate detachment.

FIGS. 5A, 5B, 5C, 5D, and 5E illustrate harvest of hESC culture in two-layer multilayer cell stacks (sodium citrate vs. EDTA).

Figure 6:
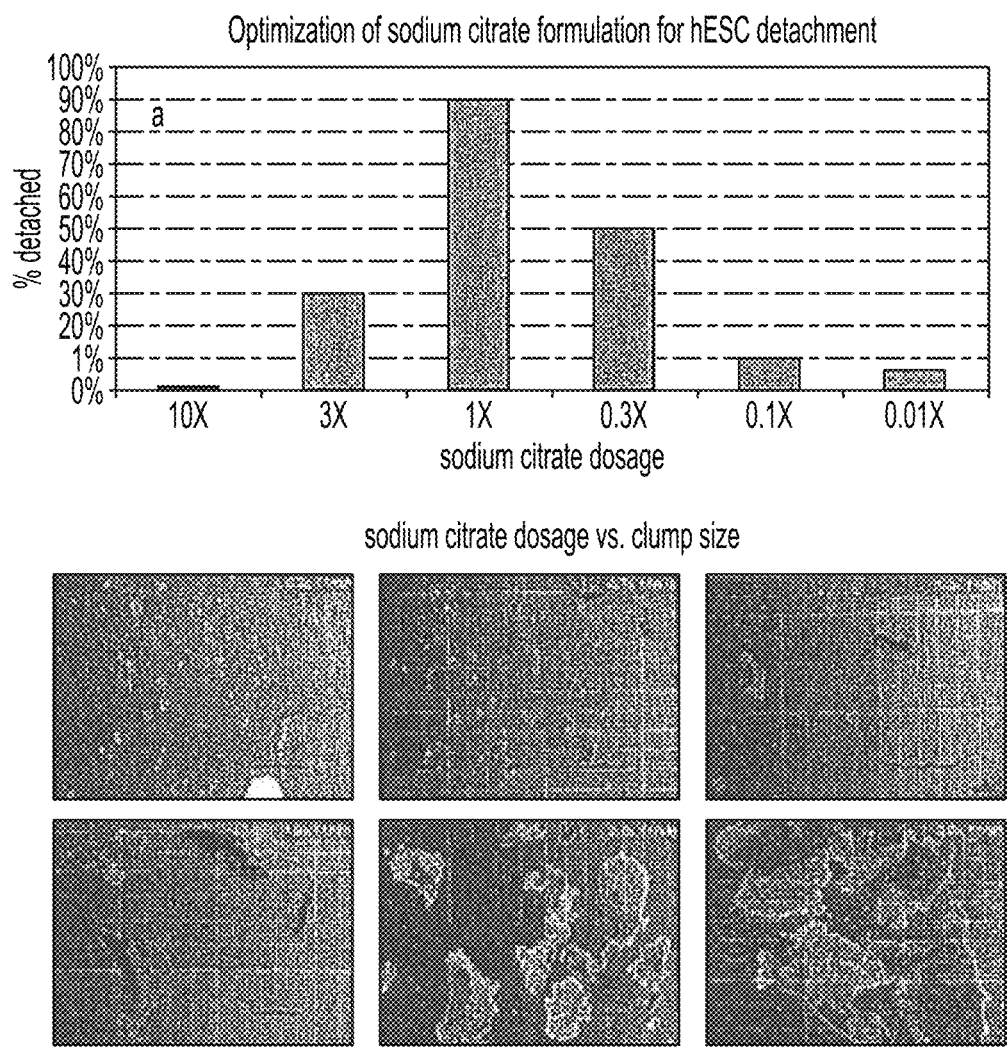

FIG. 6 illustrates optimization of sodium citrate formulation for hESC detachment.

Figure 7:
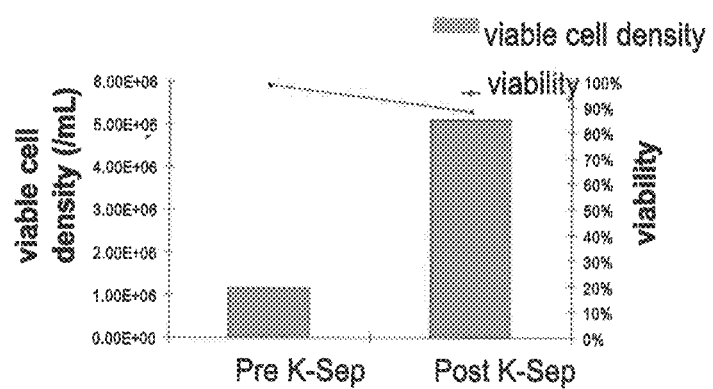

FIG. 7 illustrates the density increase of viable hESCs post-KSep processing (volume reduction) and the viability change before and after application of continuous counter-flow centrifugation technology (kSep®).

Figure 8:
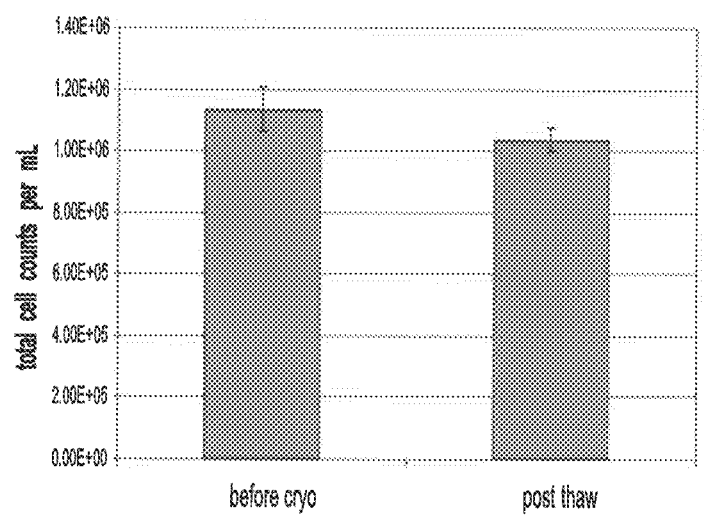

FIG. 8 illustrates the recovery of cells after cryopreservation.

Figure 9:
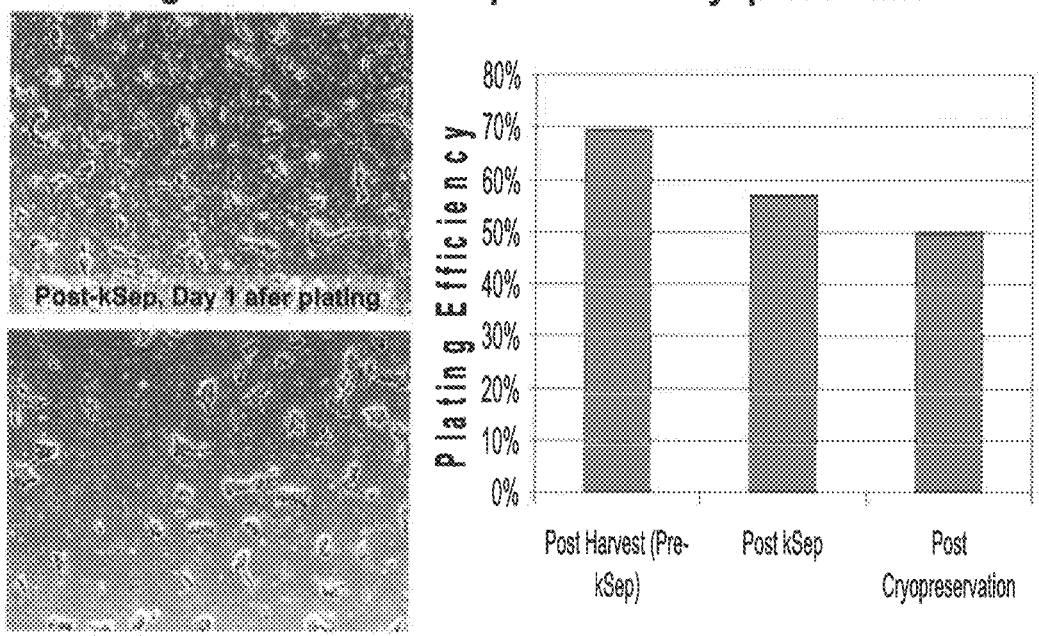

FIG. 9 illustrates re-plating of hESCs post-continuous counter-flow centrifugation technology (kSep®) and post cryopreservation.

Figure 10:
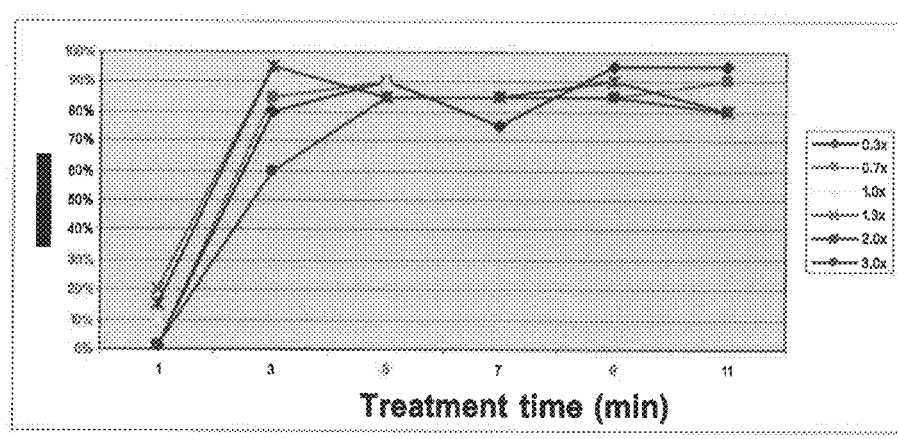

FIG. 10 illustrates the trend of increasing detachment with the increase of treatment time with various dilutions of sodium citrate formulation in MEF-CM.

Figure 11:
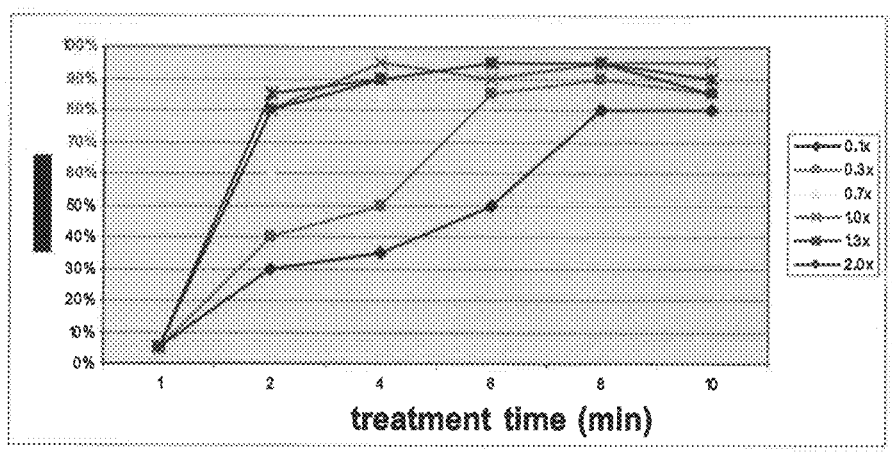

FIG. 11 illustrates the trend of increasing detachment with the increase of treatment time with various dilutions of sodium citrate formulation in mTeSR1®.

Figure 12:
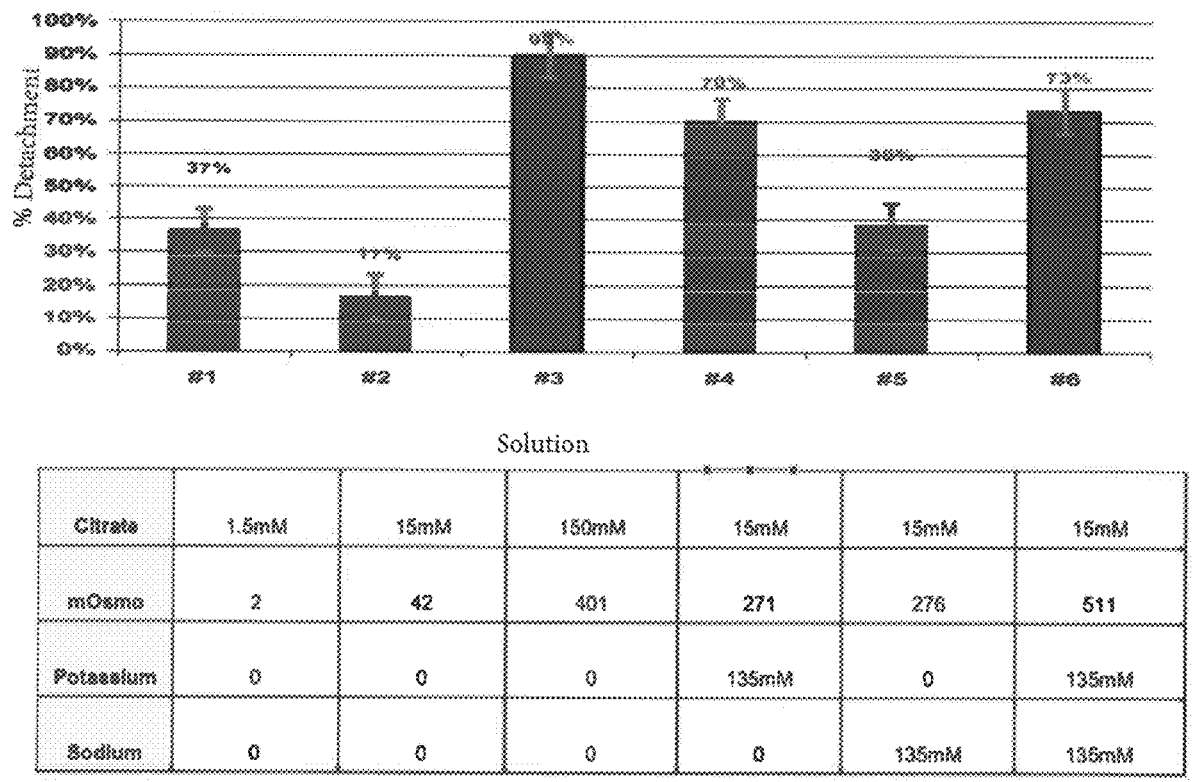

FIG. 12 illustrates the effects of osmolarity and potassium concentration on the ability of sodium citrate formulations to promote hESC detachment.

Figure 14A:
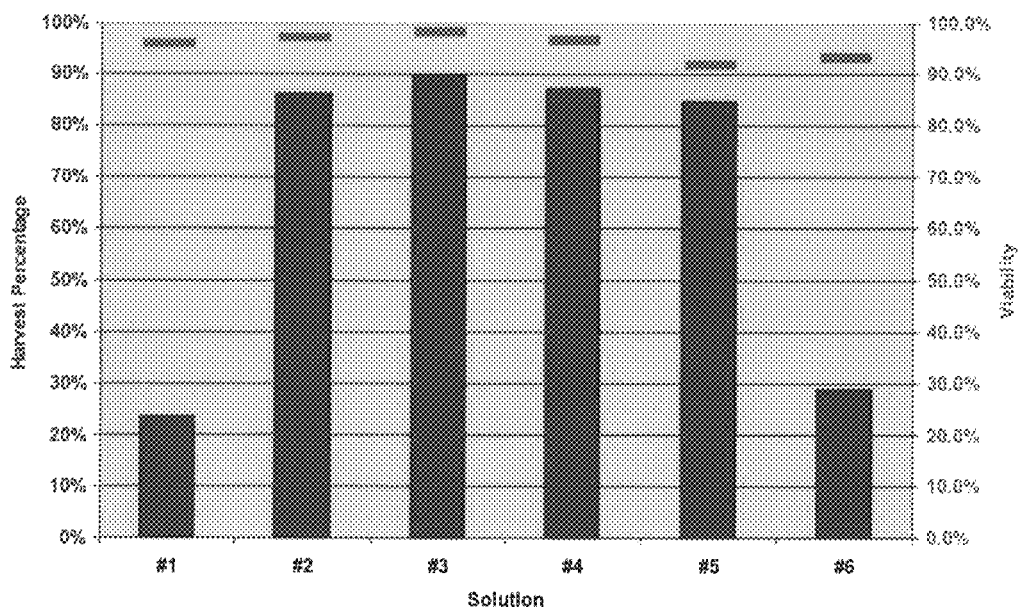
Figure 14B:
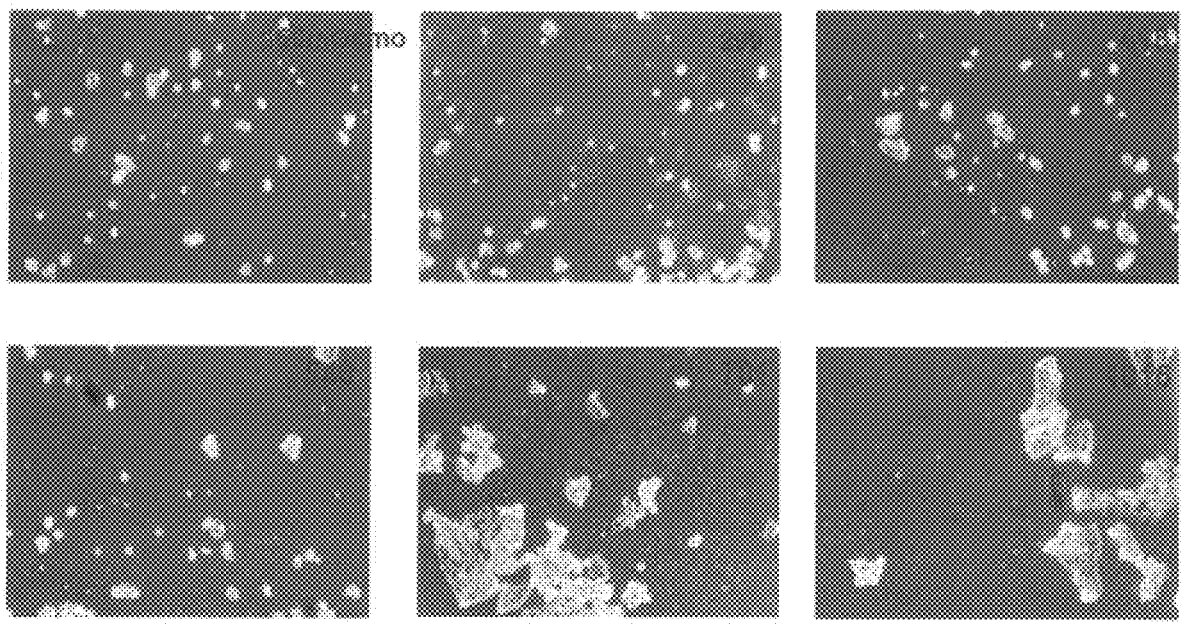
Figure 14C:
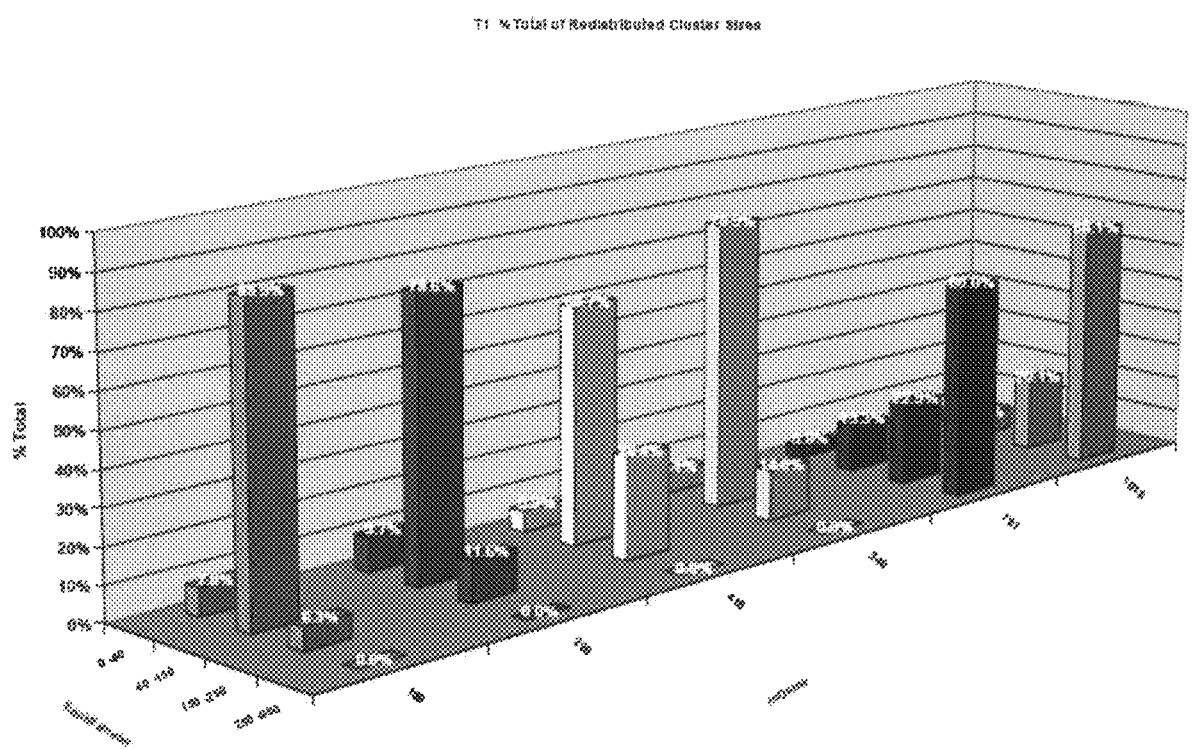

FIG. 13 illustrates the osmolarity and final concentrations of sodium citrate and KCl of various formulation solutions used in the experiments described in FIG. 14A-C.

FIGS. 14A-C illustrate the effect of osmolarity on the ability of sodium citrate formulations to promote hESC detachment and maintain large cluster size.

Figure 15A:
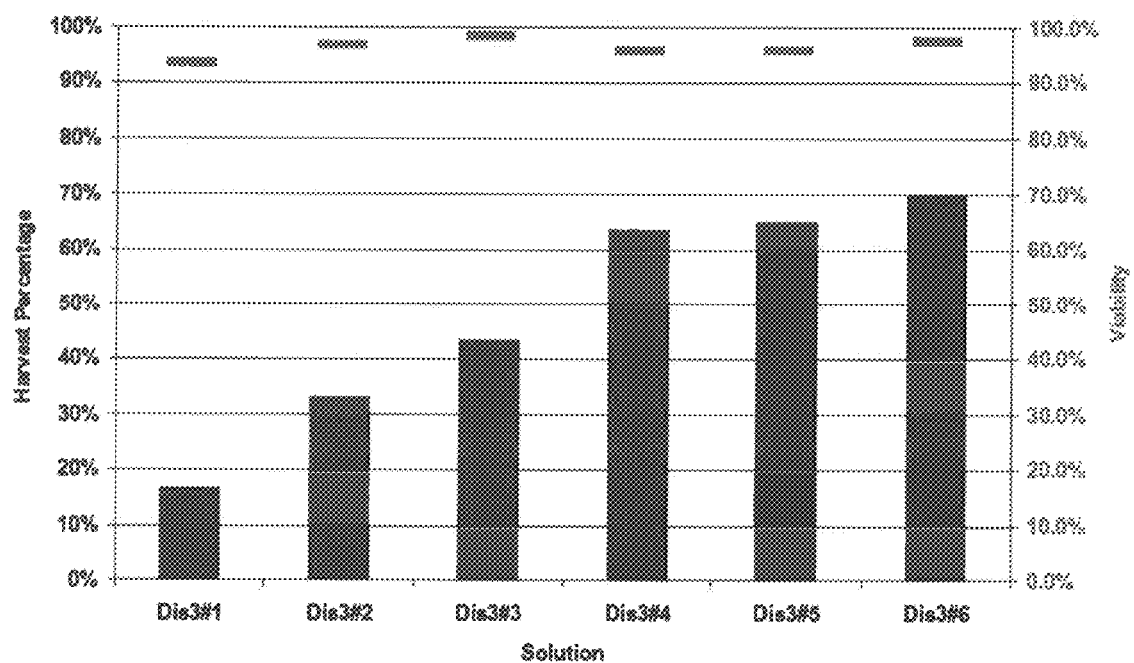
Figure 15B:
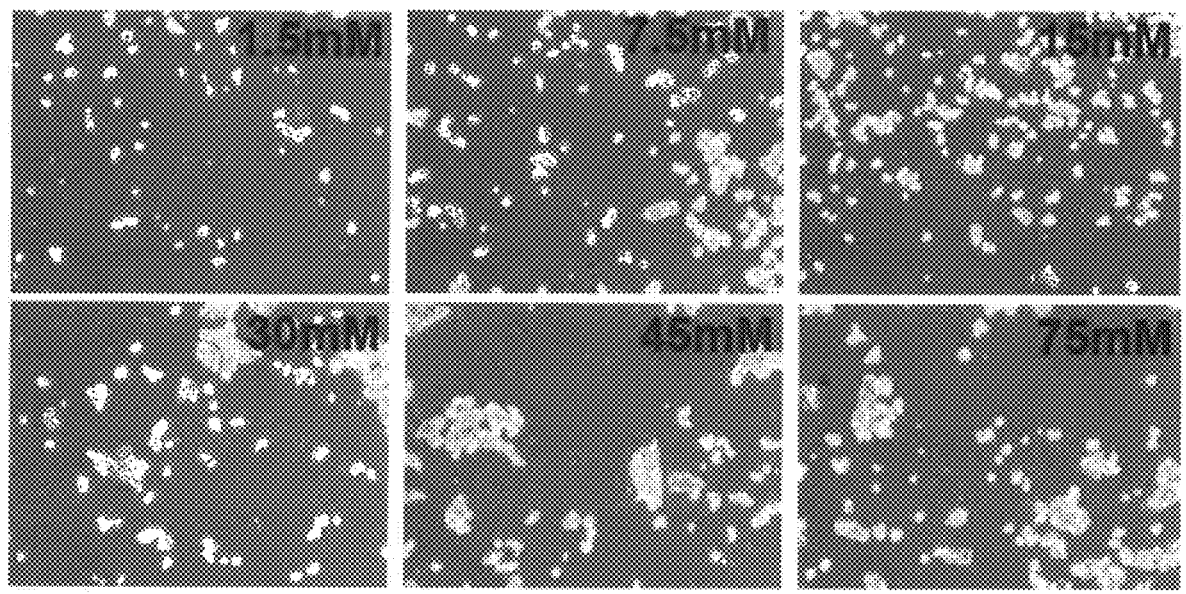
Figure 15C:
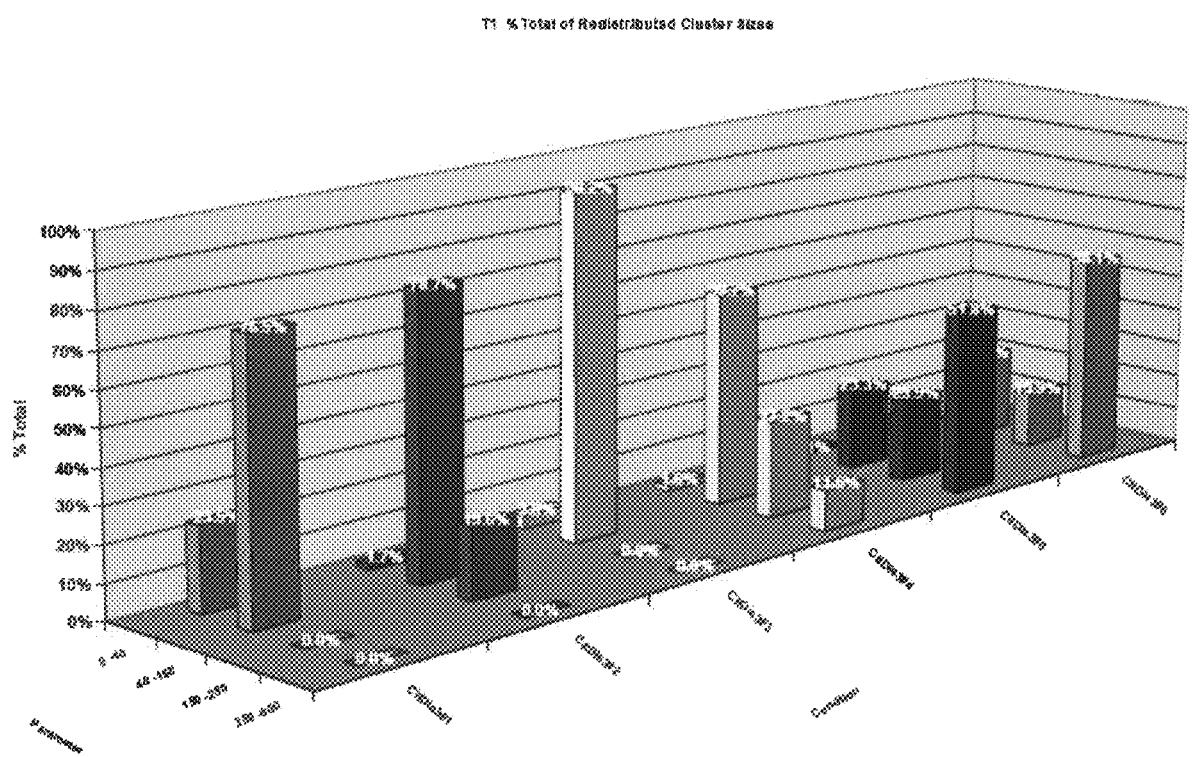

FIGS. 15A-C illustrate the effects of sodium citrate concentration on hESC detachment and on size of detached clusters.

Figure 16A:
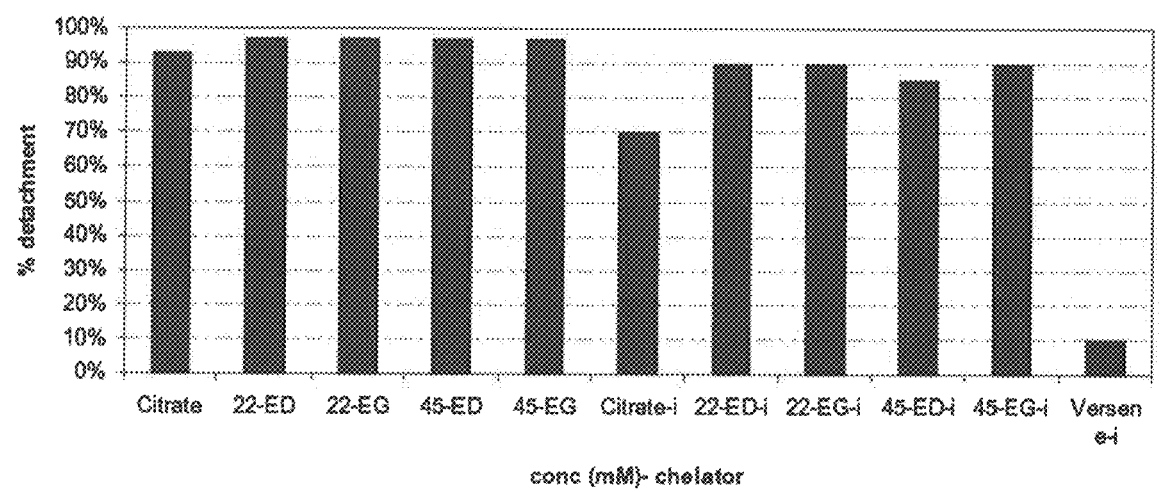
Figure 16B:
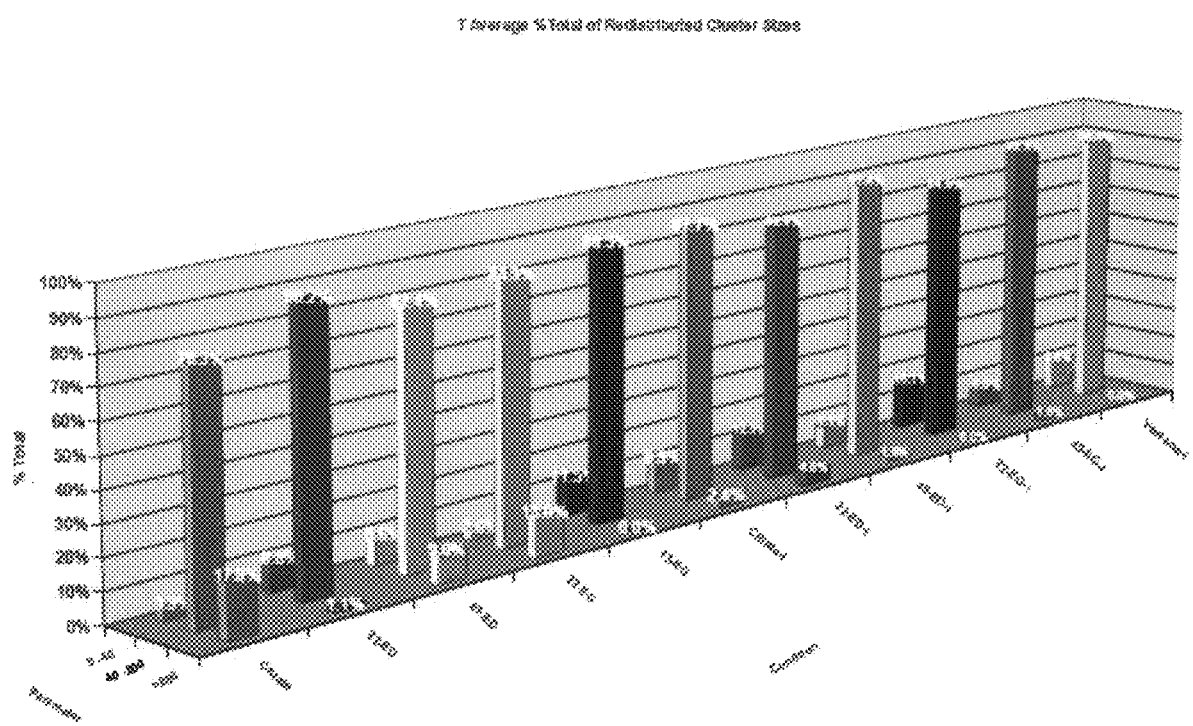

FIGS. 16A-B illustrate the effects of EDTA, EGTA, and sodium citrate on hESC detachment.

FIG. 17 illustrates formulations used in time course studies.

Figure 1:
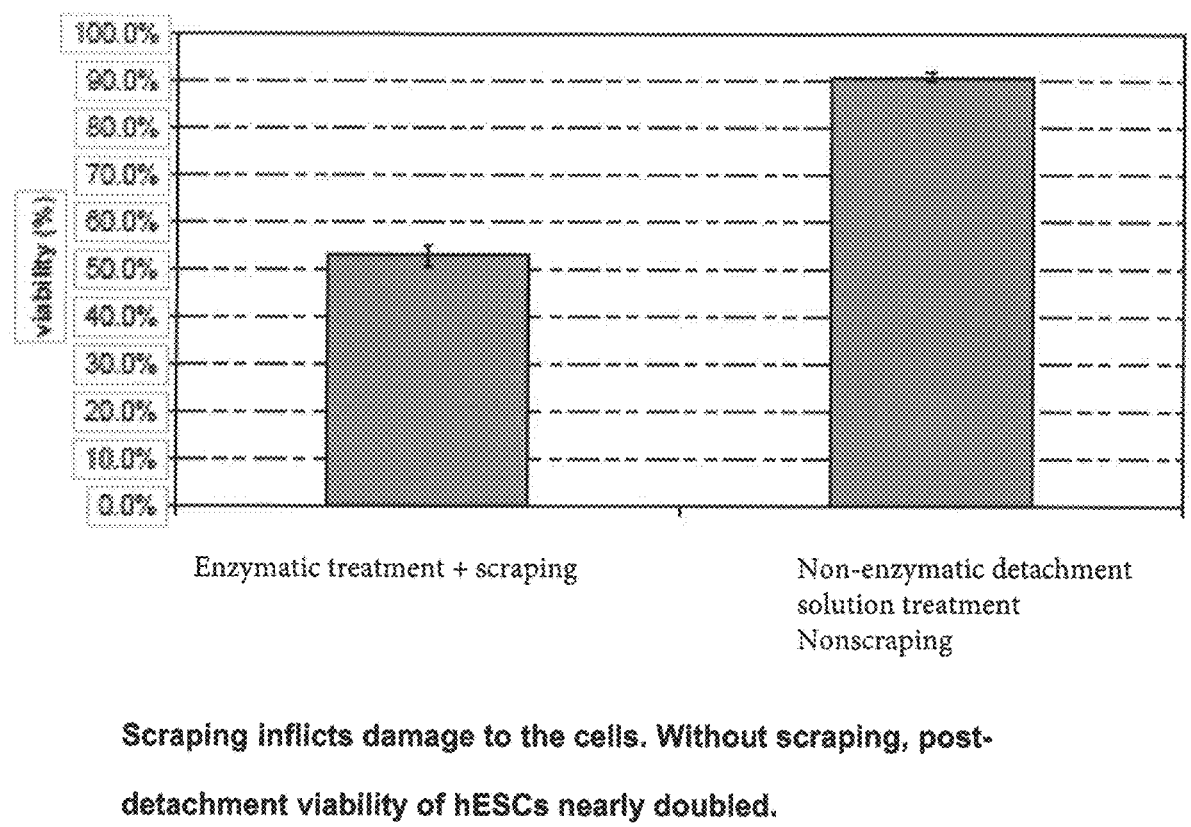
Figure 18A:
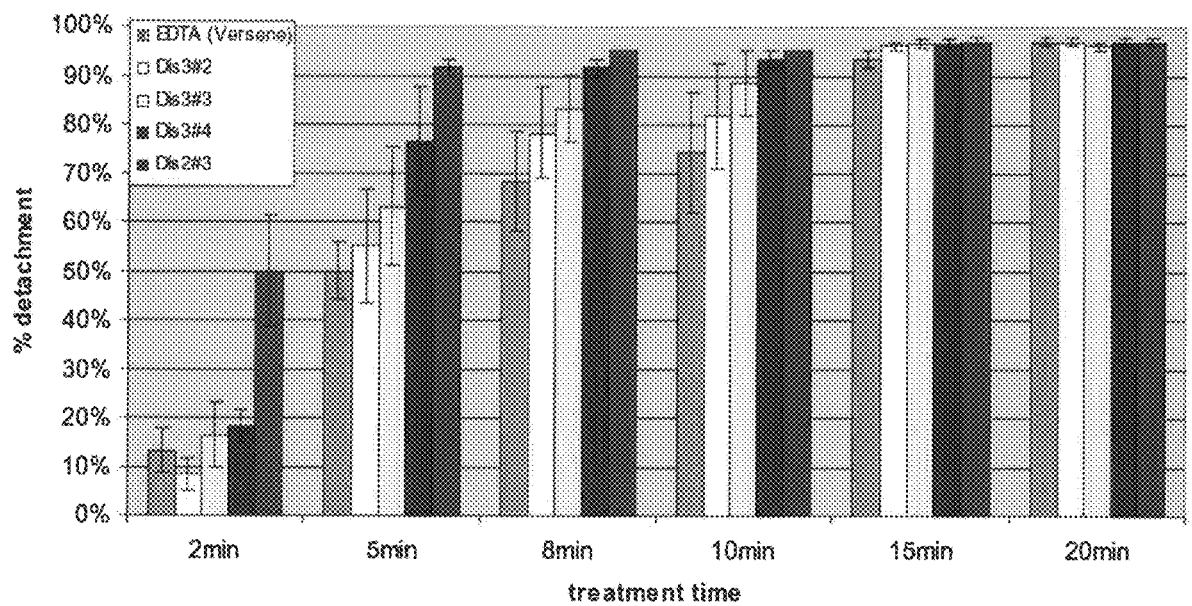
Figures 2, 18B:
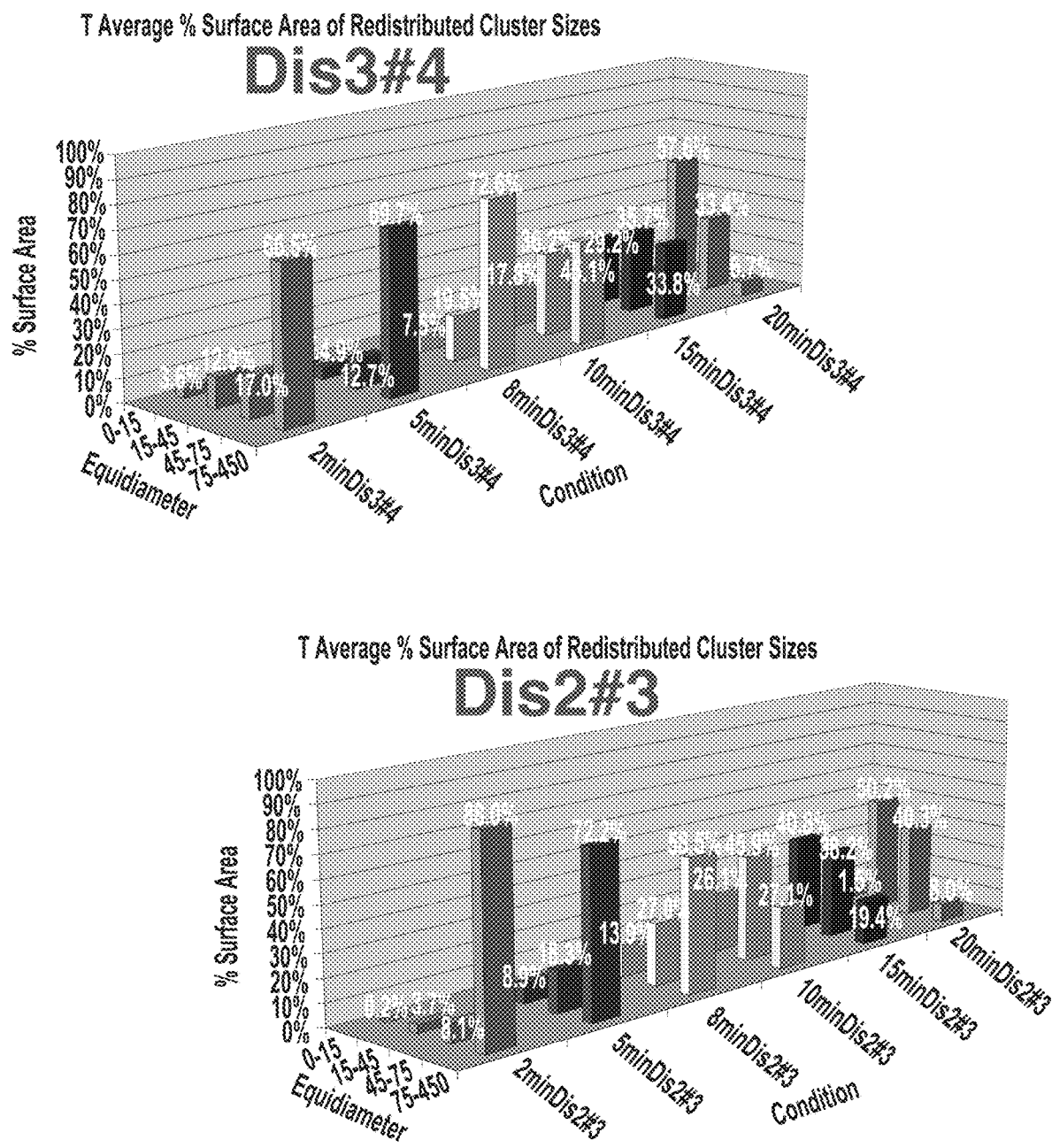

FIG. 18A illustrates the effect of treatment time with various formulation solutions on hESC detachment;

FIGS. 18B-1, and 18B-2 illustrates the size distribution of the hESC clusters detached by treatment of various sodium citrate formulations, and the effect of the treatment time on the cluster size distribution.

Figure 19:
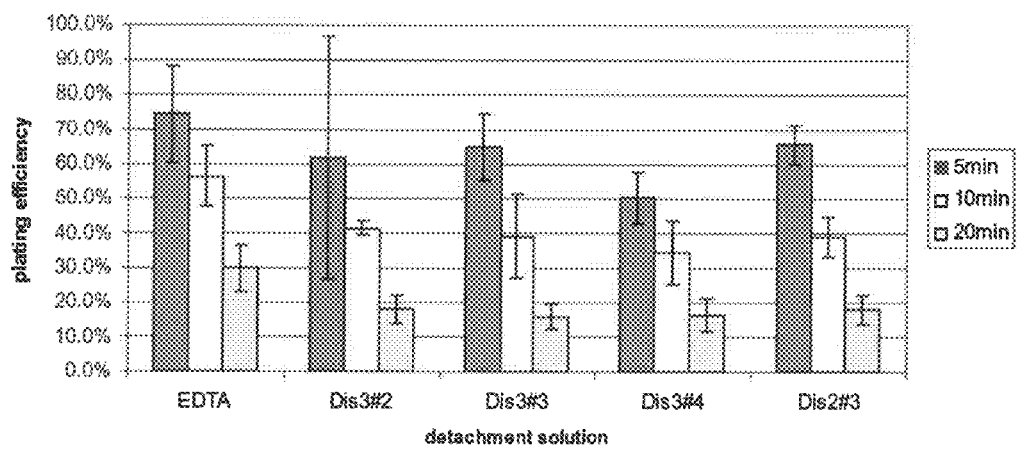

FIG. 19 illustrates the plating efficiency of hESC clusters generated using Versene® EDTA and various sodium citrate formulations, and the effect of treatment time on the plating efficiency.

Figure 20A:
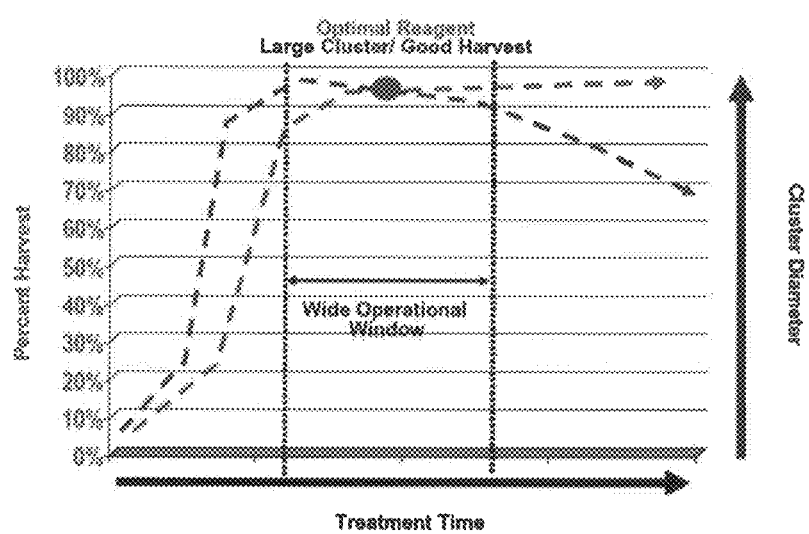
Figure 20B:
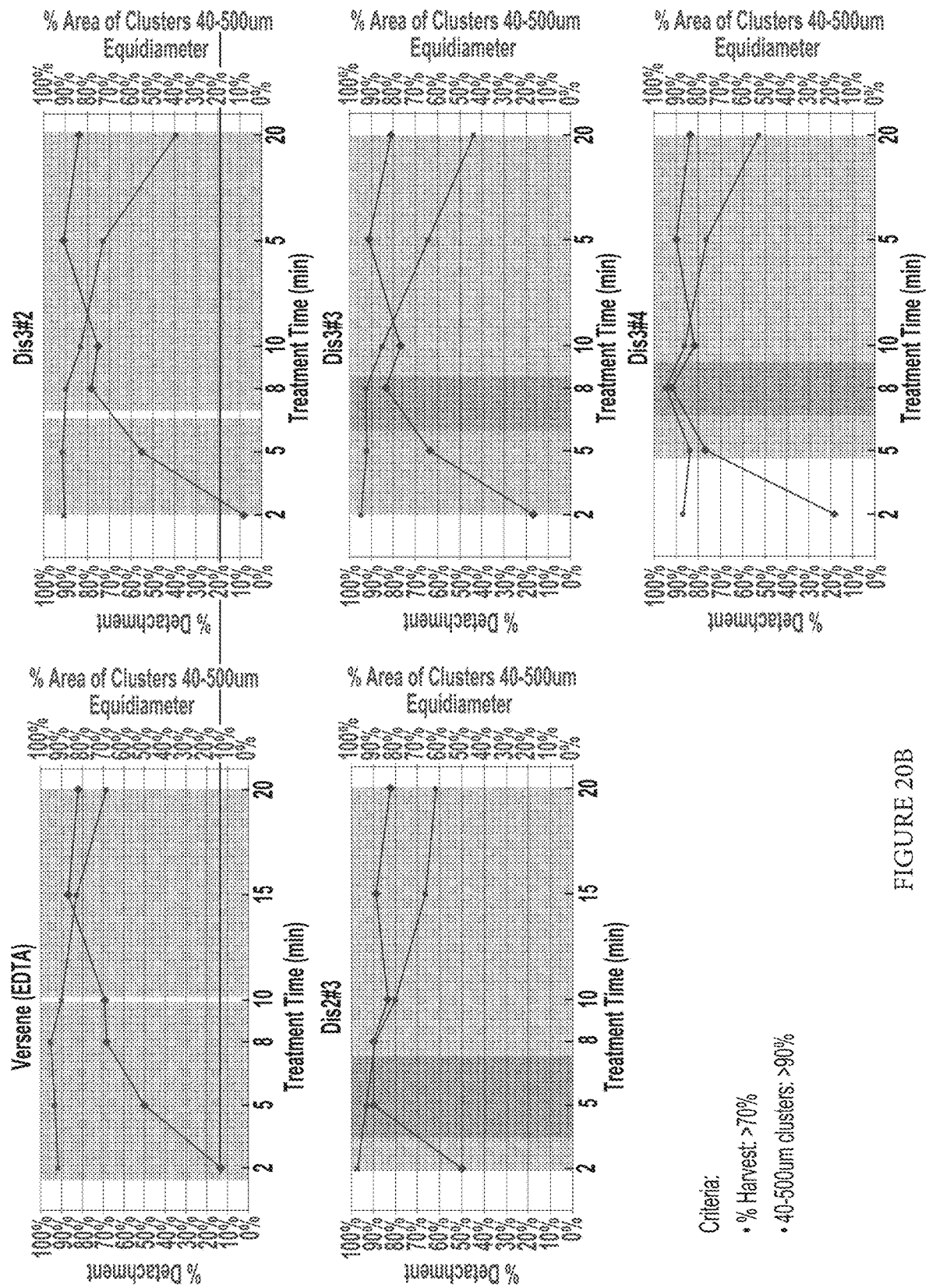

FIGS. 20A and 20B illustrate determination of the operational window (that is, time frame of treatment) to achieve optimal harvest and cluster size using cell detachment solutions.

Figure 21A:
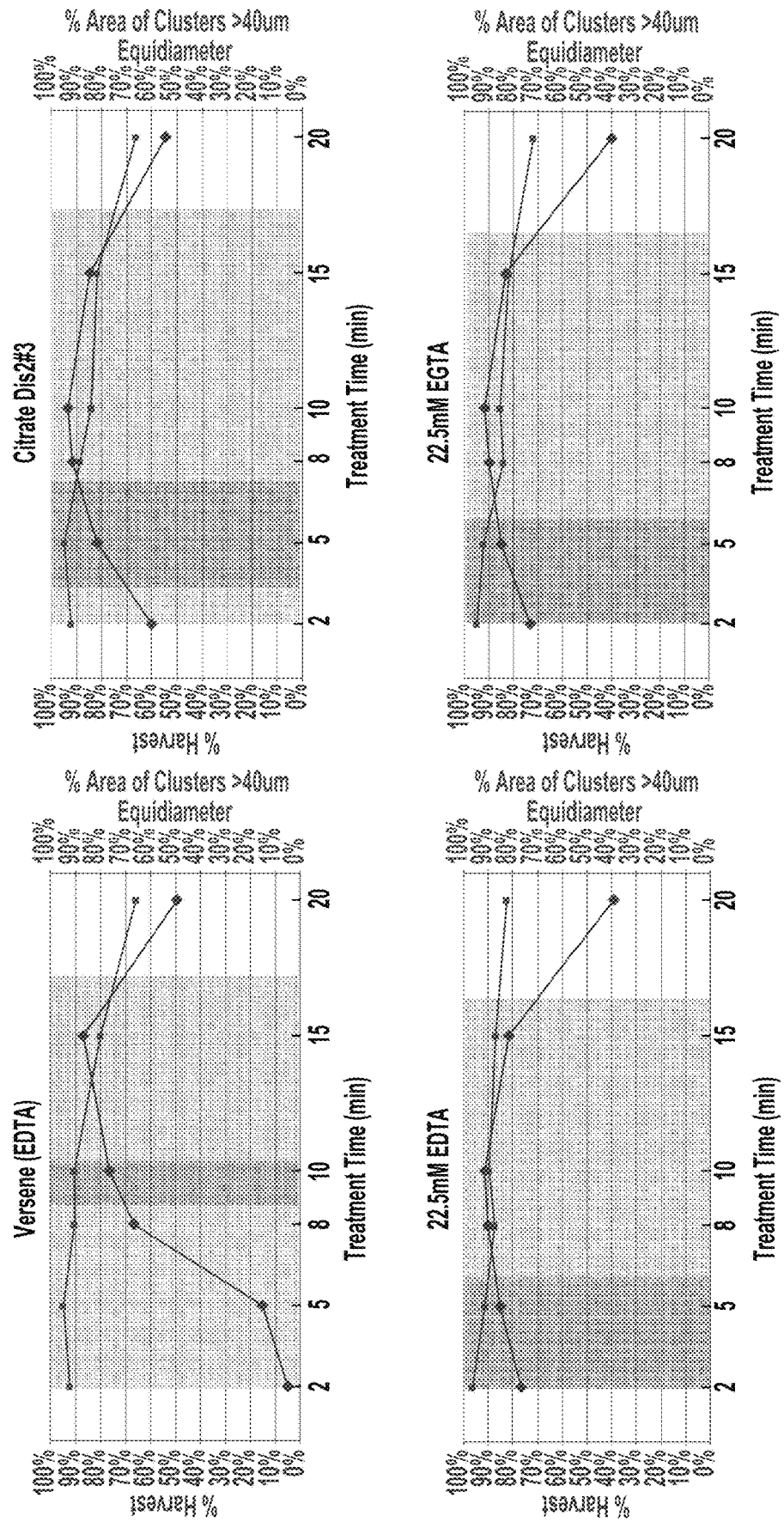
Figure 21B:
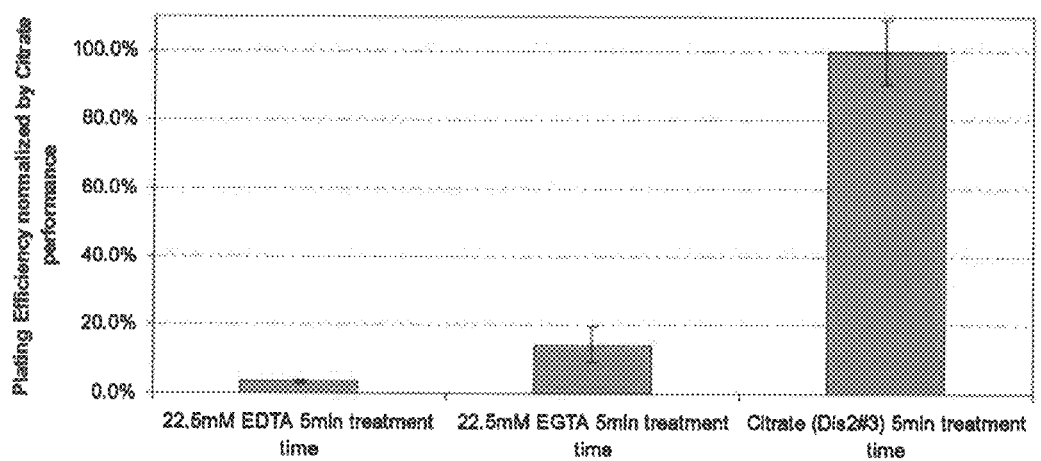
Figure 22:
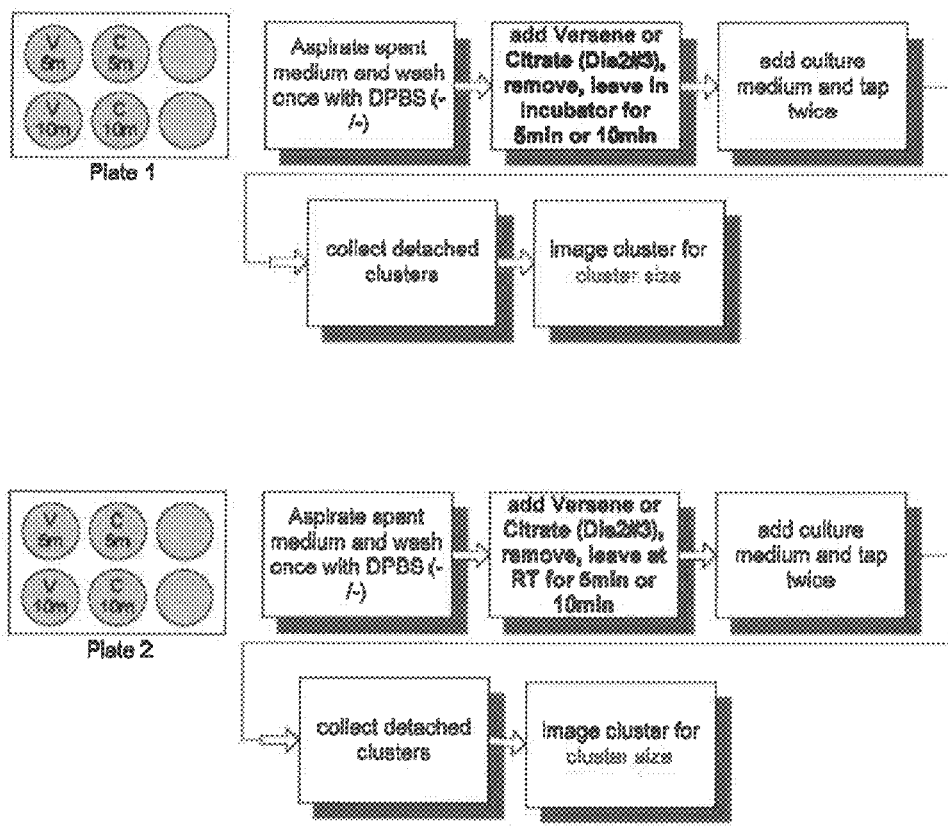

FIGS. 21A and 21B illustrate the comparison of the operational windows and the plating efficiency of hESC clusters detached using sodium citrate formulation solution with that of the clusters detached using EDTA and EGTA at high concentrations FIG. 22 illustrates the experimental procedure for harvesting hESCs from 6-well-plates using either Versene® EDTA or sodium citrate formulation solution when EDTA or sodium citrate is removed during incubation ("Dry Passaging" methodology).

FIG. 23 illustrates the chemical compositions, performance characteristics, and potential applications of three sodium citrate formulation solutions.

Figure 24:
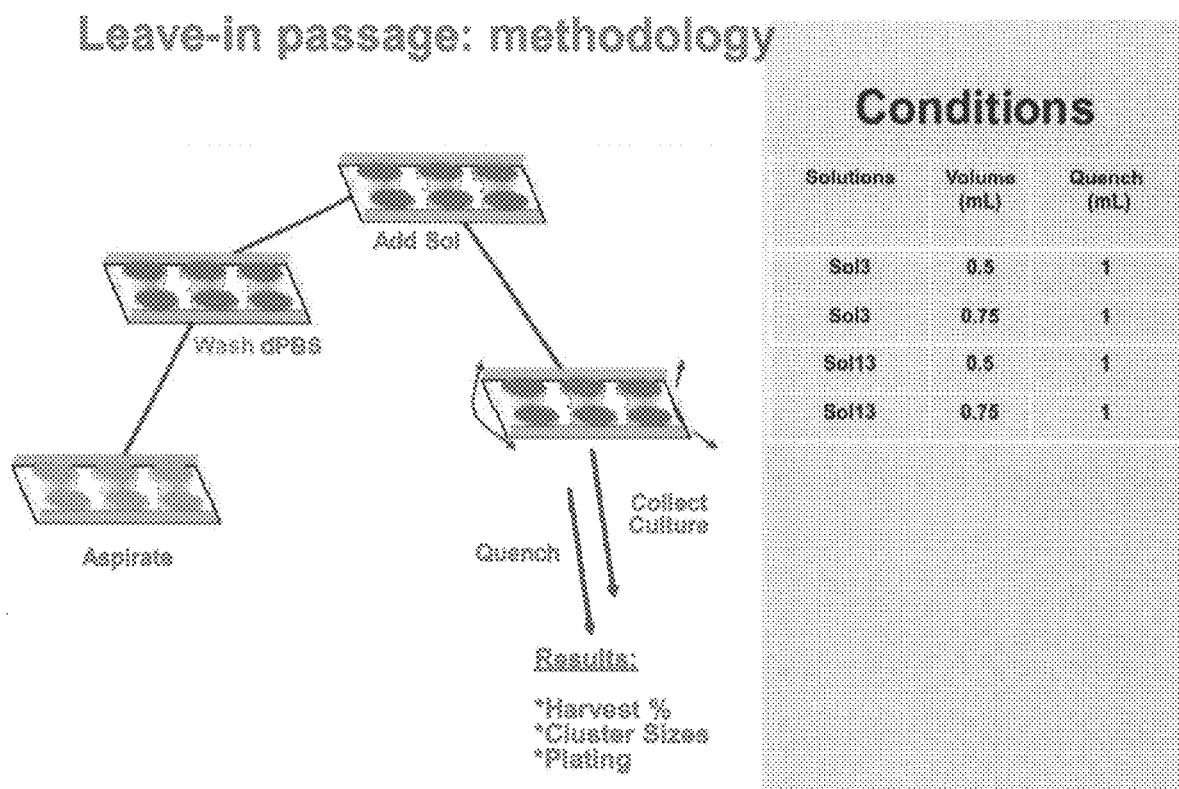

FIG. 24 illustrates the "leave-in passage" methodology.

Figure 25:
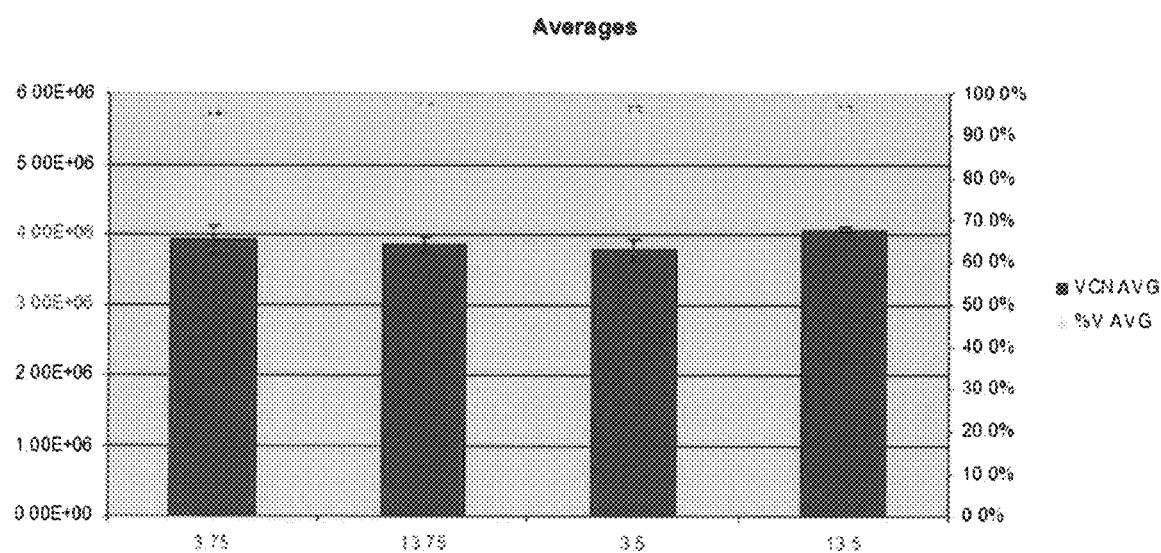

FIG. 25 illustrates the number of viable cells harvested and post-detachment viability of hESCs following "leave-in passage" with sodium citrate formulation solutions.

Figure 26:
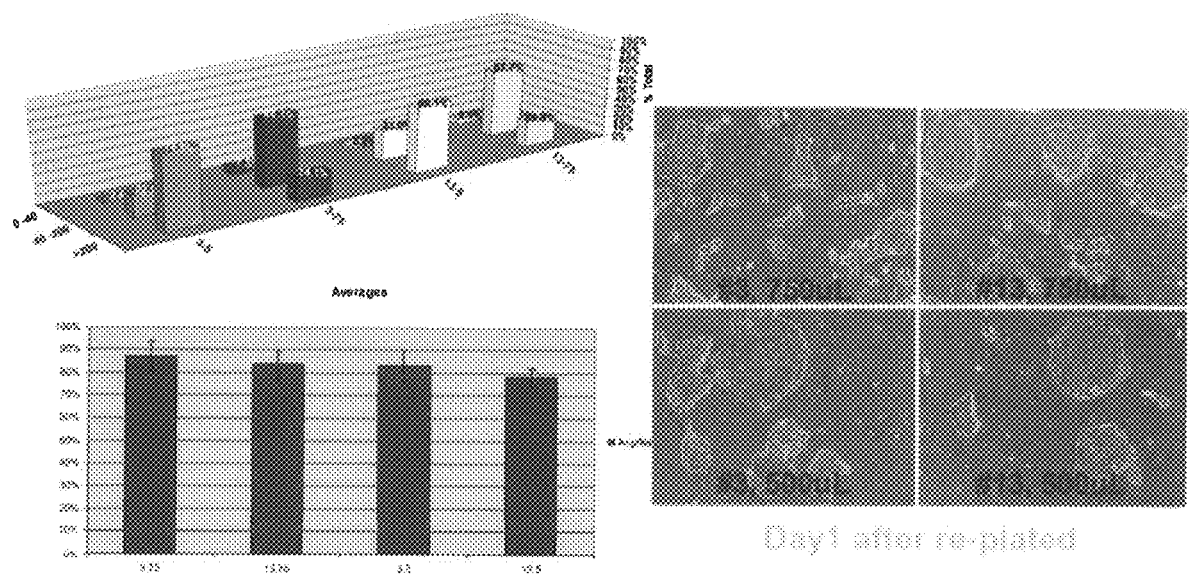

FIG. 26 illustrates the cluster size distribution, plating efficiency and the morphology of re-plated hESC colonies following "leave-in passage" with sodium citrate formulation solutions.

Figure 27:
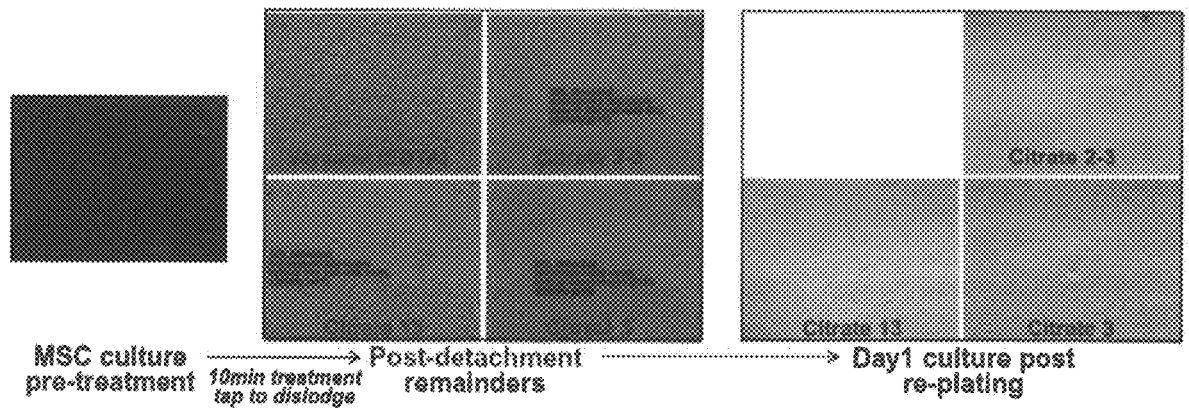

FIG. 27 illustrates the effects of Versene® EDTA and various sodium citrate formulation solutions on passaging of mesenchymal stem cells (MSC).

Figures 1, 28A:
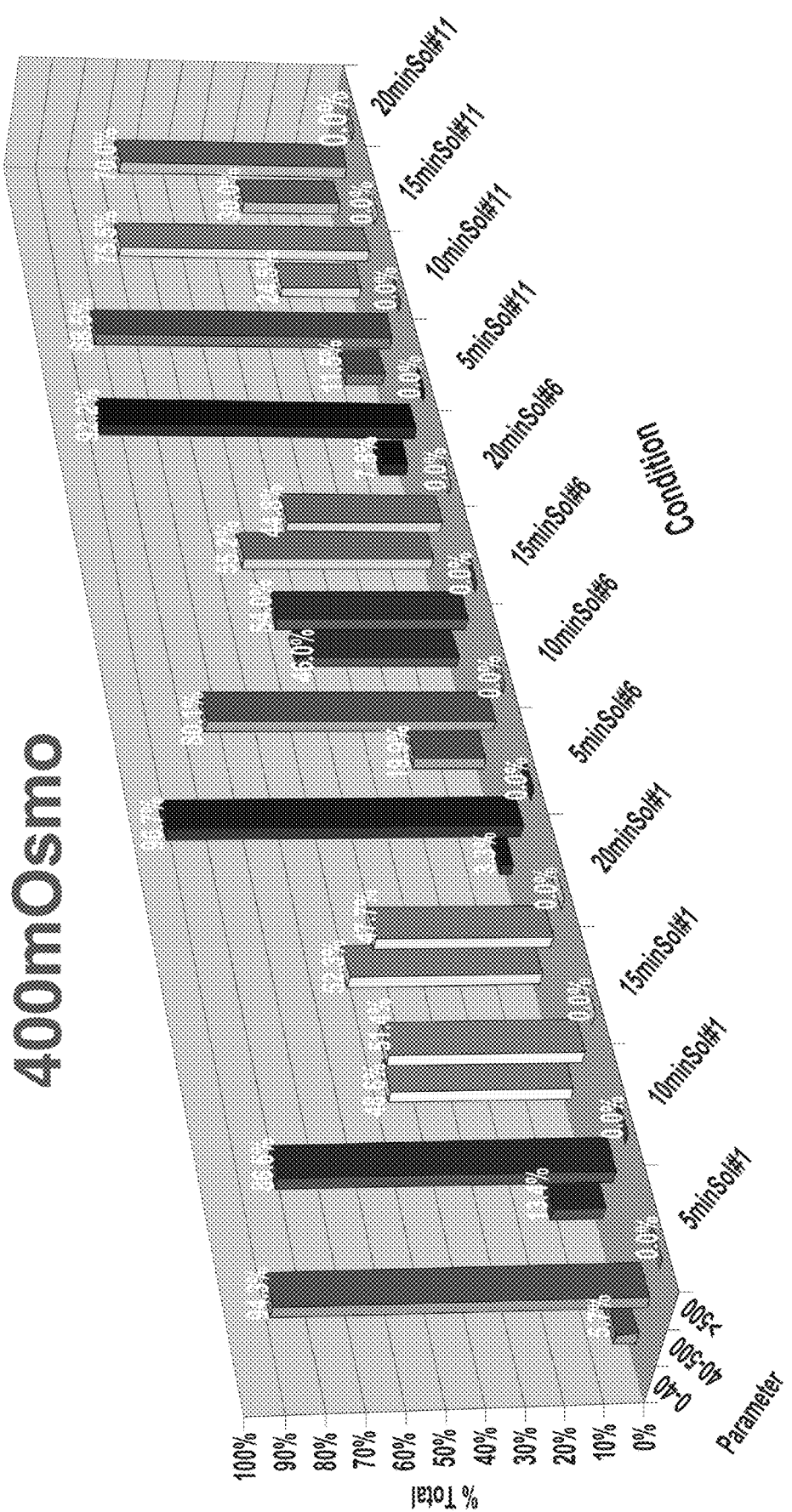
Figures 2, 28A:
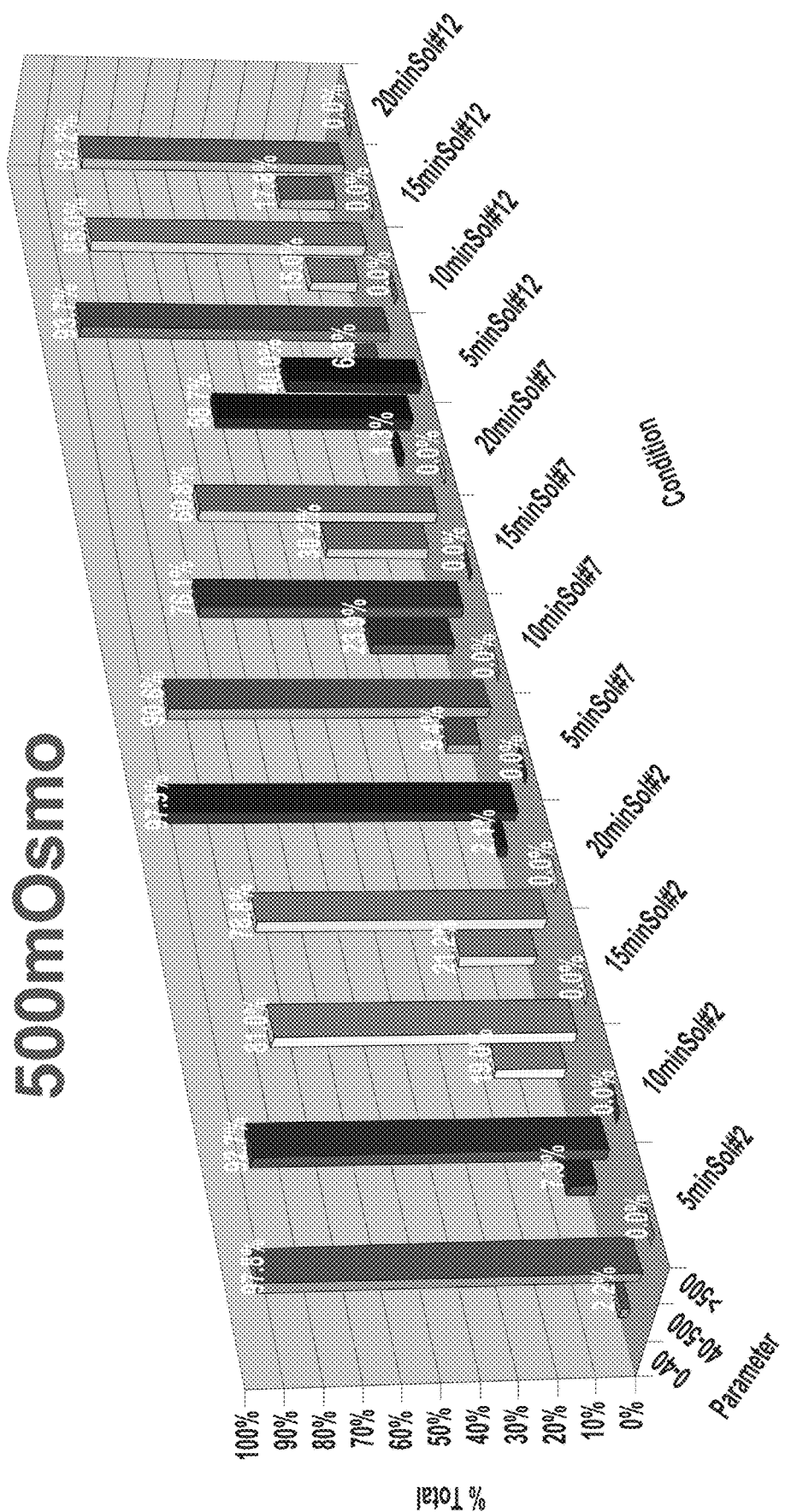

FIGS. 28A-1, 28A-2. 28A-3, 28A-4, 28A-5, 28B and 28C illustrate optimization of sodium citrate formulations towards high plating efficiency after extended treatment.

Figure 29:
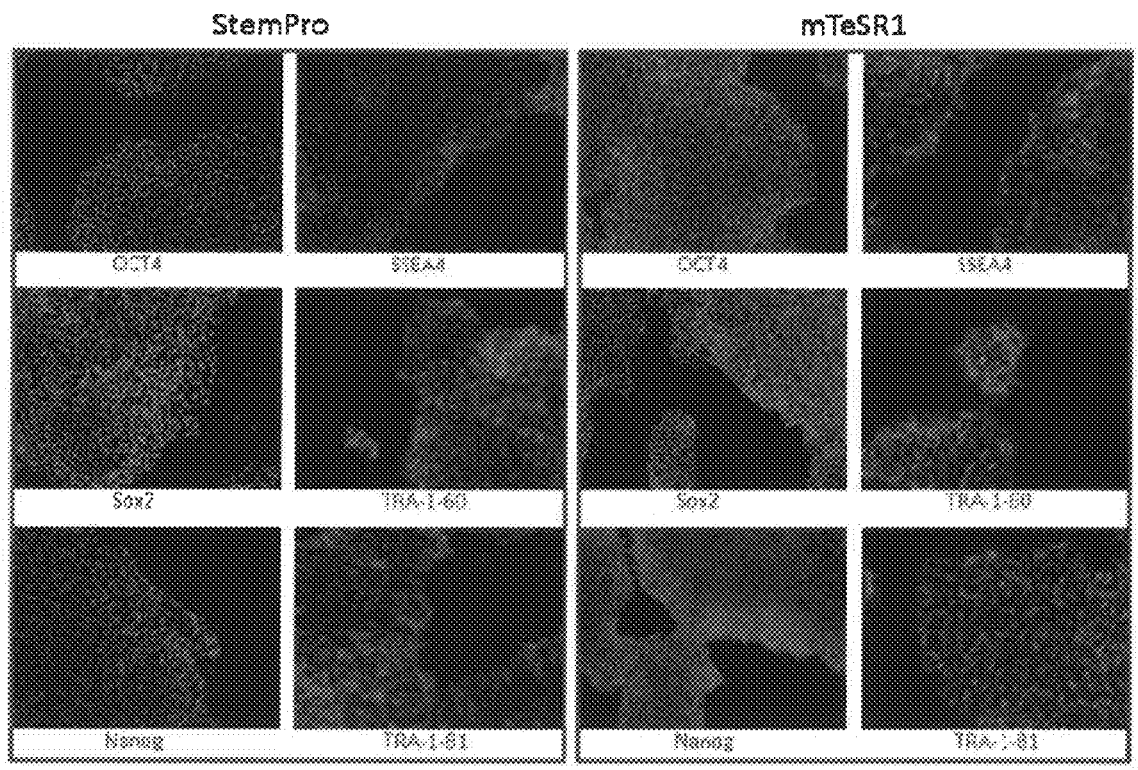

FIG. 29 illustrates the immunocytochemistry of hESC markers, as evaluation of the self-renewal of the hESCs after long-term passaging with sodium citrate formulation.

Figure 30:
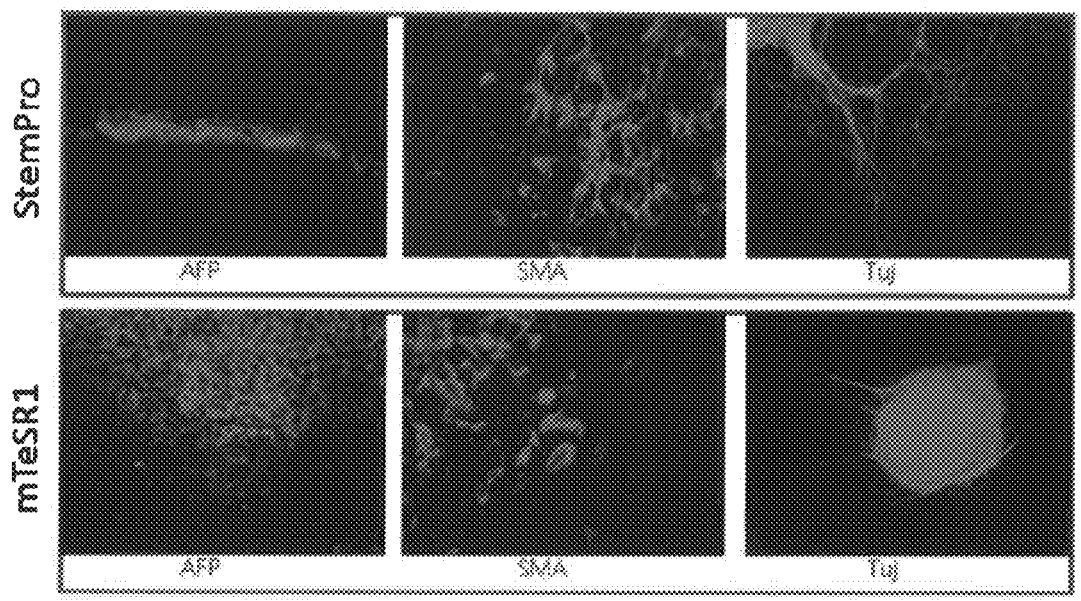

FIG. 30 illustrates the immunocytochemistry of embryoid body differentiation of hESCs, as evaluation of the differentiation capability of hESCs passaged for a long term with sodium citrate formulation.

FIG. 31 illustrates the histology of teratomas generated in immune-deficient mice injected with hESCs passaged for a long term with sodium citrate formulation, as further confirmation of differentiation capability of long-term hESC culture.

DETAILED DESCRIPTION OF THE INVENTION

Example 1

Preliminary Screening and Characterization of Various Non-Enzymatic Cell Detachment Formulation Solutions and Methods Disclosed herein is a non-enzymatic reagent formulation and a method of harvesting/passaging pluripotent stem cells as clusters with high yield and high post-detachment cell viability (>90%). These cells can then be processed as final harvest or seeded into new culture vessels to be further expanded. In one embodiment, the disclosed formulation includes sodium citrate, which disrupts the cell-surface bond and cell-cell association by chelating/sequestering $Ca^{2+}$, the divalent cation required for cell-surface and cell-cell binding. This sodium citrate-based formulation and process is specially designed and developed to address the unique challenges in routine or scale up hPSC culture and manufacturing processes. hPSCs are normally passaged as multicellular clusters/aggregates, and passaging hPSCs as single-cells is to be avoided due to low cloning efficiency of hPSCs and the high risk of karyotypic abnormality. This formulation and method is additionally optimized for harvesting and passaging hPSCs in reference to the key quality parameters of hPSCs, for example, viability, yield, post-detachment cluster size, passageability, and maintaining a pluripotent phenotype. This formulation and process can be used in any hPSC lab as routine lab practice to expand hPSC culture with reduced labor intensity and process time. For example, this formulation and process does not require mechanical scraping to get the cells off the surface and the cell harvest does not need to be washed and centrifuged to remove the agents used to detach the culture. This formulation and process especially benefit large-scale hPSC production when the cells are growing in multilayer cell culture vessels where scraping cannot be applied. Using this formulation and method, more than 90% of hPSCs grown in multilayer cell culture vessels can be harvested with more than 90% viability.

A variety of non-enzymatic cell detachment solutions at various concentrations were screened with one objective being to improve the yield of hESCs harvested from multilayer culture vessels while retaining the simplicity of the Versene® EDTA harvesting/passaging method. This screening included, for example, Versene® EDTA solutions at 0.1, 0.55, 1, 3, and 10 mM, Versene® based ethylene glycol tetraacetic acid (EGTA) solutions at 0.1, 0.55, 1, 3, and 10 mM, and 1× sodium citrate solution (10× solution: 0.15 M sodium citrate, 1.35 M potassium chloride (KCl), diluted to 1× in $Ca^{2+}/Mg^{2+}$-free DPBS).

All of these reagents (EDTA, EGTA and sodium citrate) are $Ca^{2+}$ chelators and have been used historically for detaching adherent cells in culture. As mentioned previously, Versene® EDTA has been used routinely for harvesting/passaging hESCs in some labs; both EDTA and EGTA (in combination with trypsin) were used to passage hESCs in a study published by Thomson et al. at Roslin Institute in Scotland in 2008 (Thomson et al. (2008), "Human Embryonic Stem Cells Passaged Using Enzymatic Methods Retain a Normal Karyotype and Express CD30", Cloning and Stem Cells, 10 (1), 1-17.).

hESCs cultured in Murine Embryonic Fibroblast-conditioned medium (MEF-CM) were treated with solutions including those described above as follows: (1) remove culture medium; (2) wash once with $Ca^{2-}/Mg^{2+}$ free buffer (for example, DPBS); (3) incubate in solution at room temperature; (4) remove solution; and (5) soak the colonies in MEF-CM for 0.5-1 minute to let them have a chance to stick back onto the surface. The colonies were then hosed with culture medium to see if they can be detached from the surface. Related to incubation step #3 above, it is noted that 4-9 minutes is the norm for Versene® EDTA. It is generally longer with culture grown in undefined serum or serum replacement-containing medium (for example, MEF-CM), and shorter in defined serum-free medium such as mTeSR1®. Thus, an incubation window of 2-12 minutes is contemplated. Treatment for more than 9 minutes can result in the generation of too many single cells. Treatment for less than 2 minutes can be too short a time frame resulting in partial detachment. Sodium citrate solution (1×) can detach the cells grown in mTeSR1® in 2-3 minutes, and detach the cells grown in MEF-CM in 3-4 minutes.

Related to step #5, this step was executed in the initial detachment-solution screening study to see whether the cells re-stick onto the surface in culture medium. For harvesting cells grown in an open platform such as 6-well plates, the cells are hosed off the surface right after removing the cell-detachment solution. However, for multilayer cell culture vessels, after draining out the detachment solution, the culture medium is poured into the vessel first, the medium is leveled in all layers, and then the vessel is tapped to dislodge the cells in the culture medium. In one embodiment, the pouring and leveling take 0.5-1 minute in a ten-layer vessel. In the cGMP setting, additional time may be required. A portion of the culture is inevitably soaked in the culture medium during these steps and may re-stick onto the surface. As mentioned previously, this is a difficulty with the use of Versene® EDTA, which results in the incomplete detachment/harvest of the culture in multi-layer cell culture vessels. Therefore, soaking the colonies in culture medium for 0.5-1 minute was done to evaluate the re-sticking of the cells onto the surface.

Figure 2A:
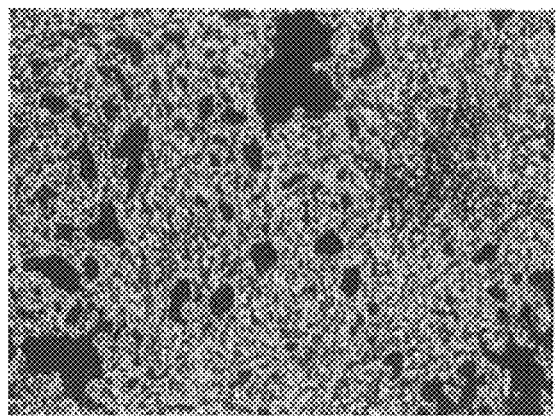
Figure 2B:
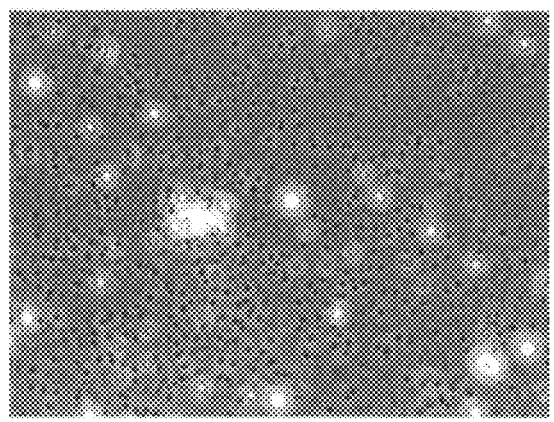
Figure 2C:
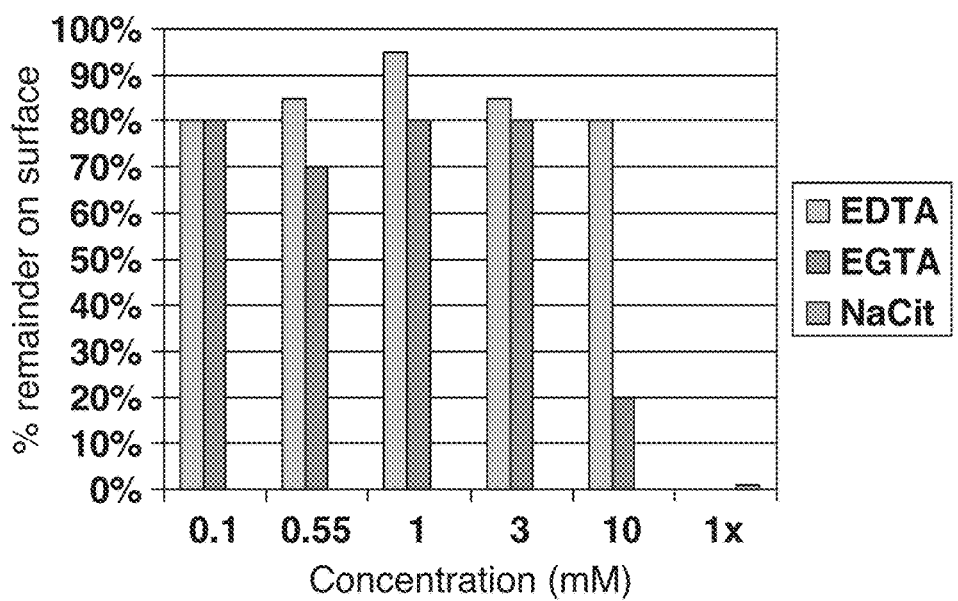

As illustrated by FIGS. 2A, 2B, and 2C, after this procedure, 85% of the Versene® (0.55 mM EDTA)-treated culture remained on the surface (FIG. 2A), while nearly all the cells came off the surface in 1× sodium citrate (sodium citrate formulation) treated culture (FIG. 2B). The visual assessment of the percentage of the culture remaining on the surface after treatment is plotted in FIG. 2C. Through this experiment, sodium citrate solution is surprisingly identified as a superior reagent compared to Versene® EDTA for harvesting hESC culture. Sodium citrate formulation disrupts the cell-surface bond to a greater extent than Versene® EDTA and sodium citrate formulation treated hESCs do not re-stick to the surface in culture medium as fast and easily as Versene® EDTA or EGTA formulation-treated hESCs.

Two commercially available solutions were tested as potential solution to harvest hPSCs out of multilayer cell culture vessels. One was from Millipore, the "PBS Based Enzyme-Free Cell Dissociation Solution", the other was "Hank's Based Enzyme-Free Cell Dissociation Solution". Both of the solutions contain EDTA, Glycerol and Sodium Citrate. When used on H9 hESCs cultured in MEF-CM, neither one of the solutions was able to detach the cells effectively.

Figure 4:
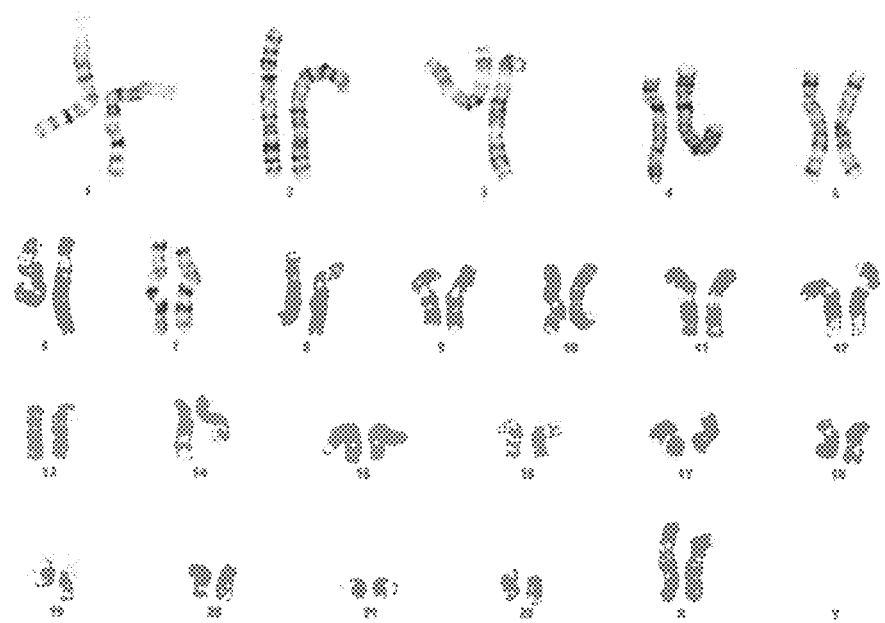
FIG. 4 illustrates the normal karyotype of hESCs passaged five times following harvesting with sodium citrate.
Figures 3, 28A:
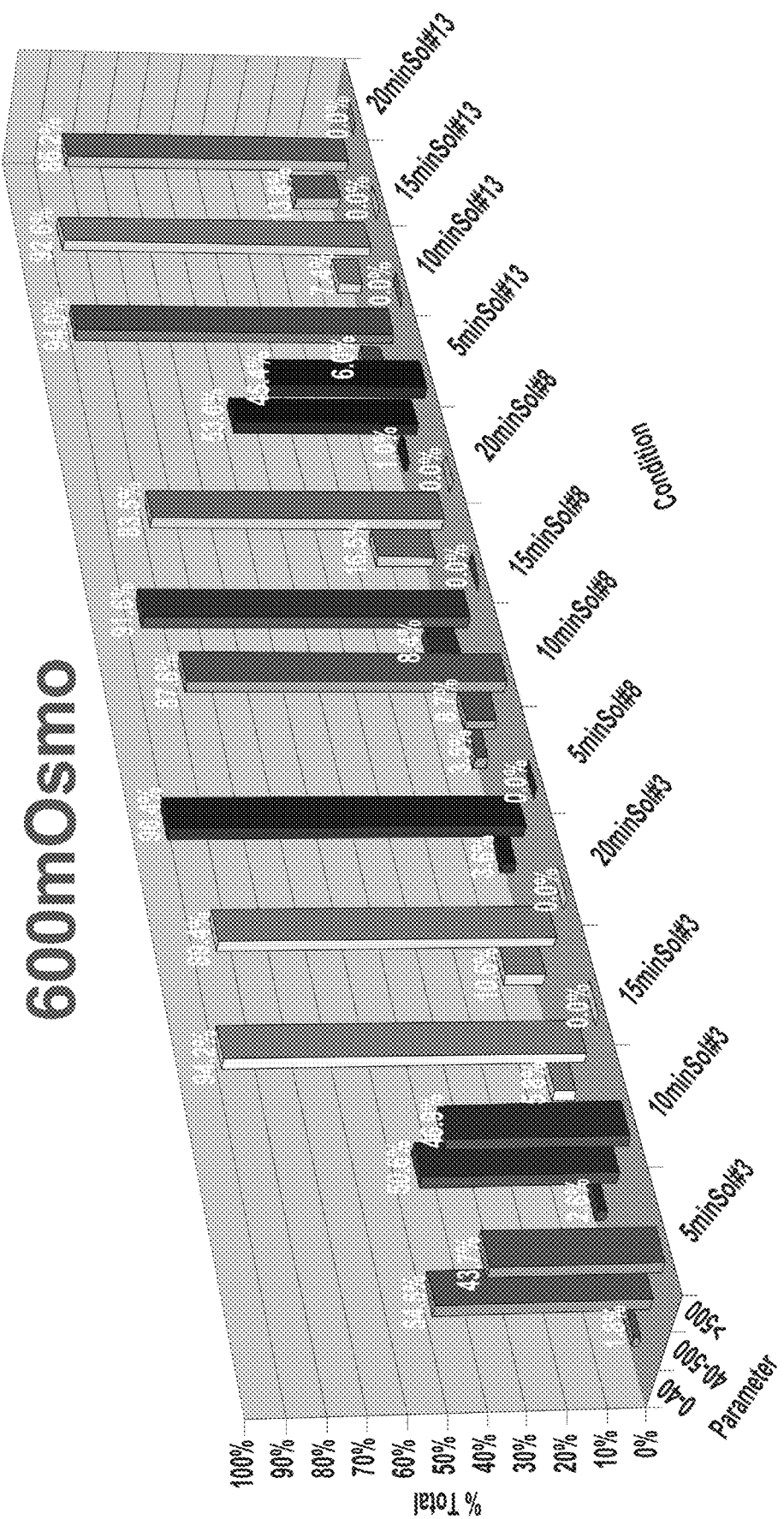
FIG. 3 illustrates hESCs continuously passaged with sodium citrate showing typical hESC colony morphology and growth.
Figures 4, 28A:
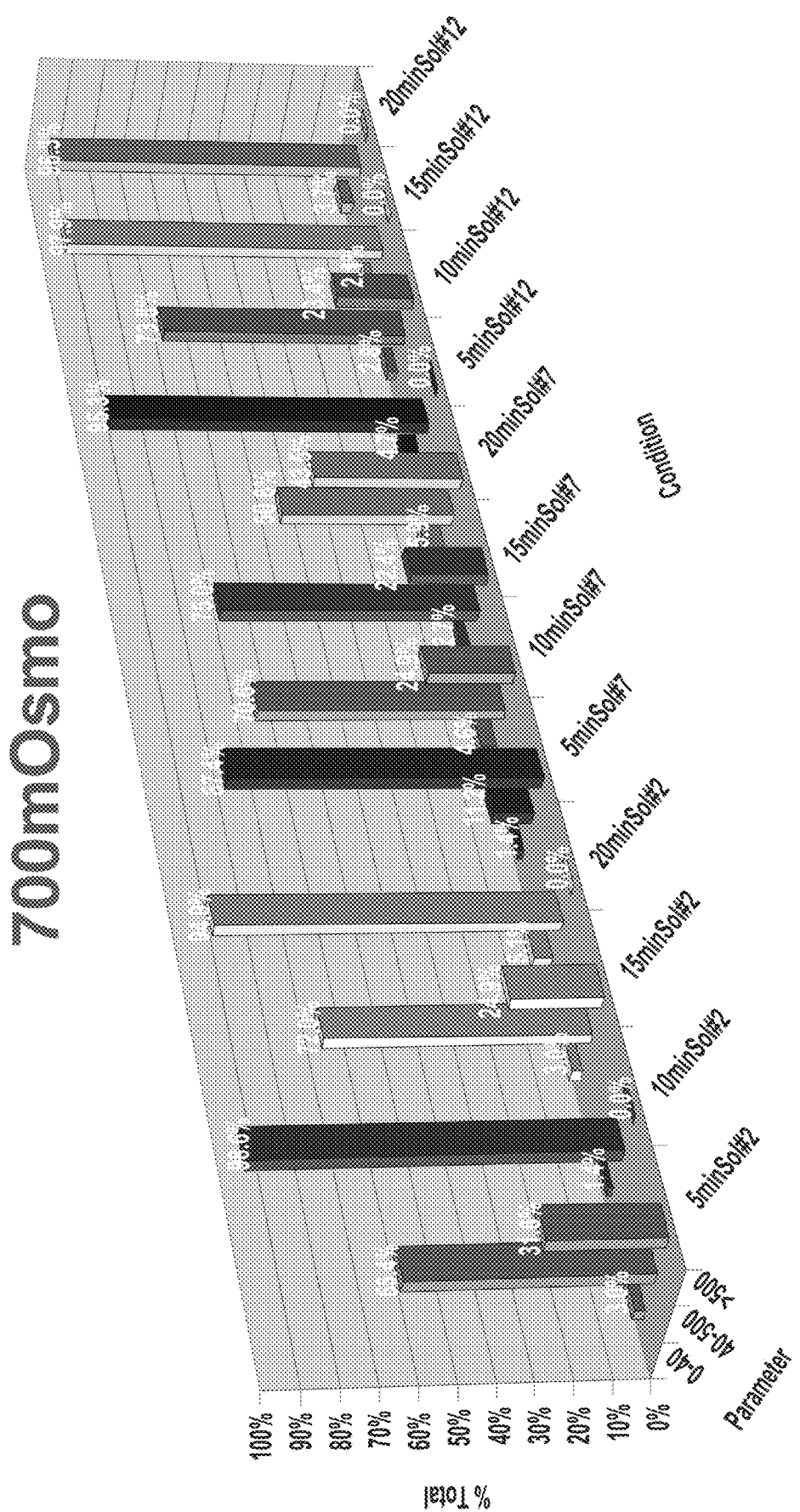
Figures 5, 28A:
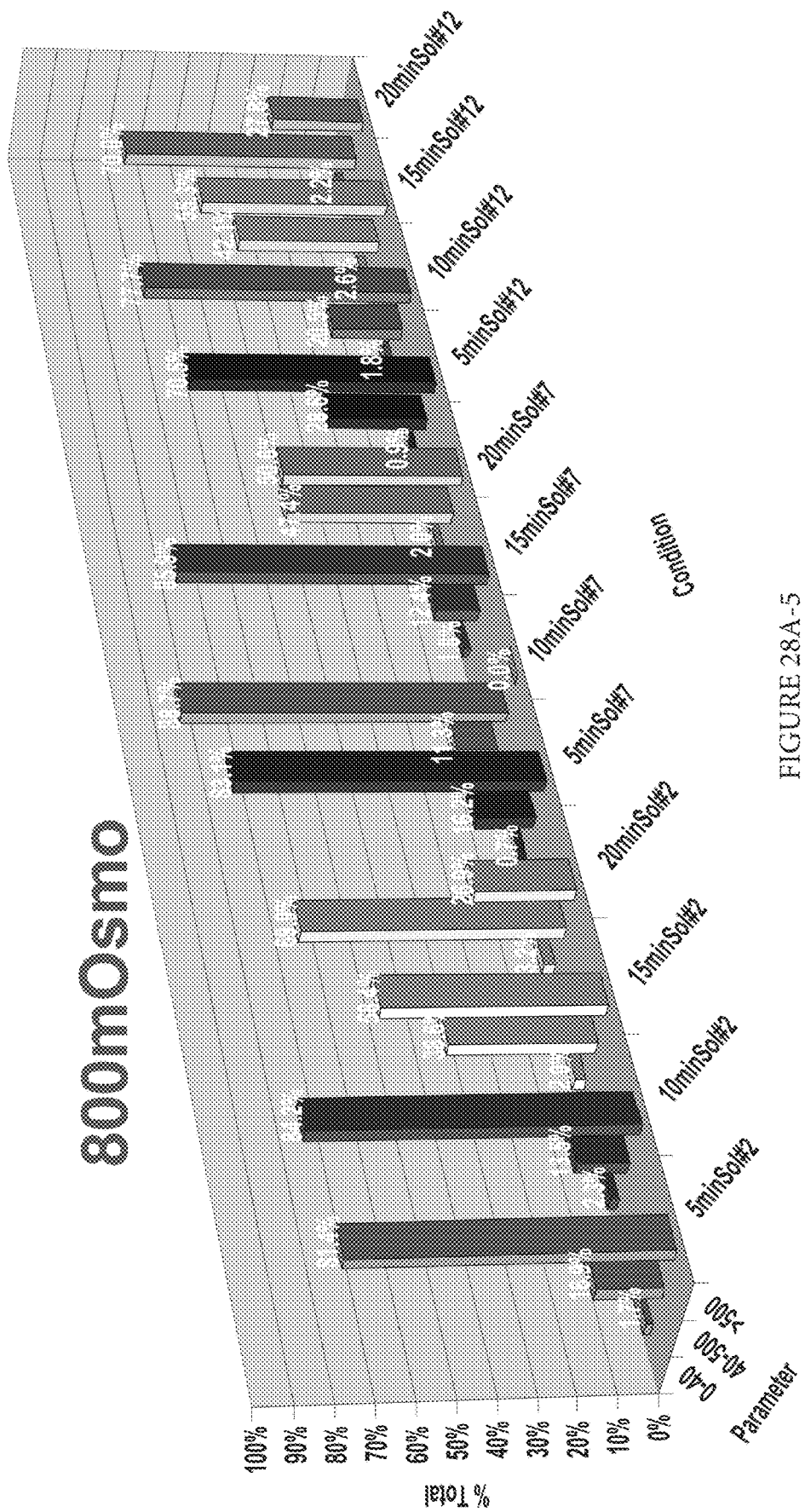
Figure 28B:
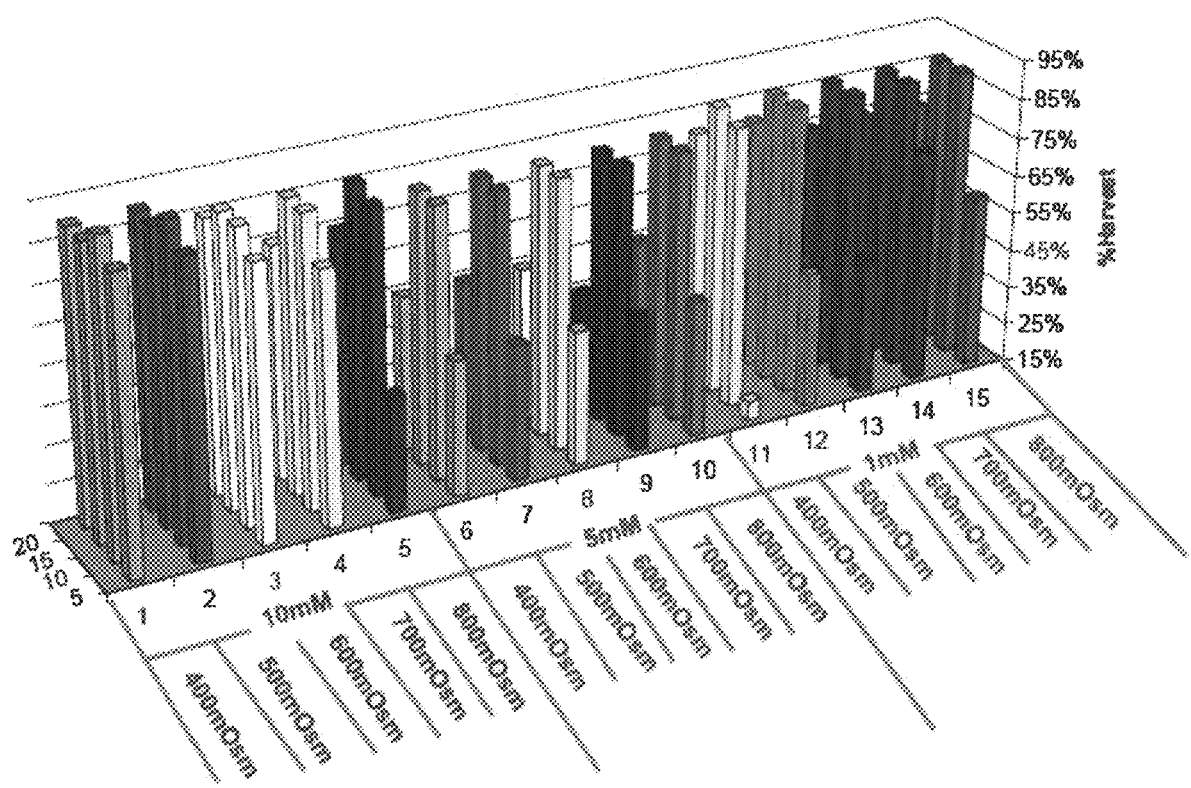
Figure 28C:
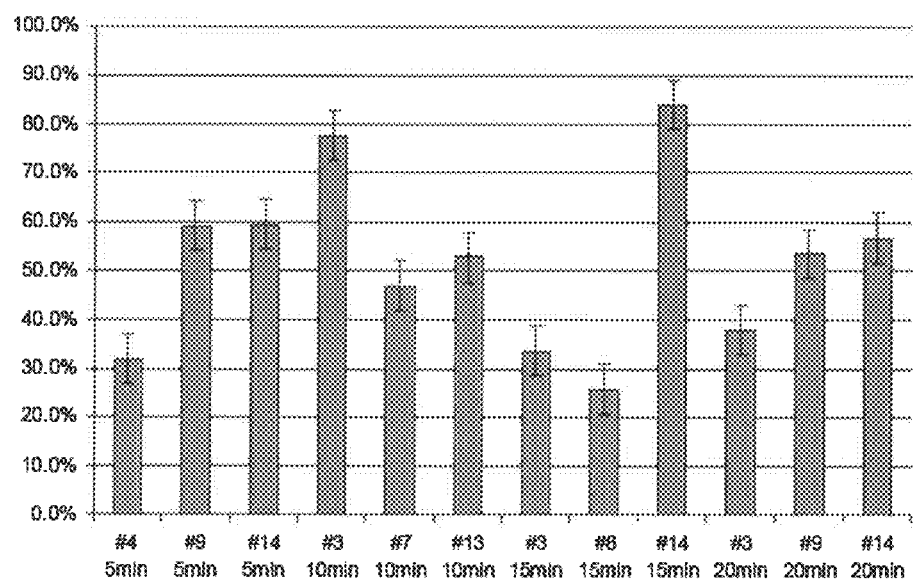

Further experimentation was performed to determine whether sodium citrate formulation can be used to passage hESC cultures; that is, whether hESCs detached by sodium citrate formulation can be plated onto a fresh surface to start a new culture. In one exemplary experiment, hESCs treated with sodium citrate formulation were continuously passaged six times in MEF-CM and three times in mTeSR1®. FIG. 3 shows that hESCs passaged with sodium citrate formulation for six times in MEF-CM retain typical hESC morphology. As illustrated by FIG. 4, the karyotype of this culture was evaluated to be normal after five passages with sodium citrate formulation. Further testing has confirmed normal karyotype at 10 passages in MEF-CM, 29 passages in mTeSR1®, and 25 passages in StemPro®. It is contemplated that a normal karyotype will be present at greater than 50 passages.

Figure 5A:
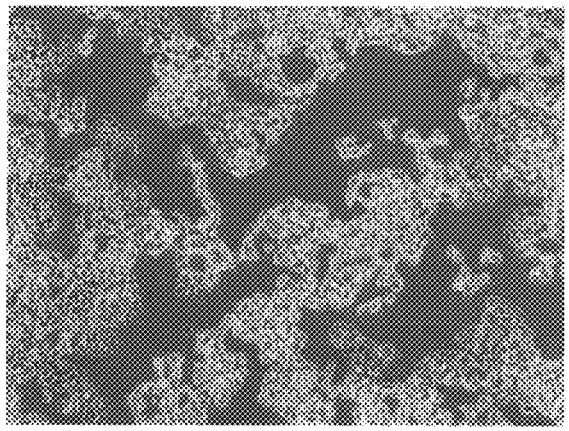
Figure 5B:
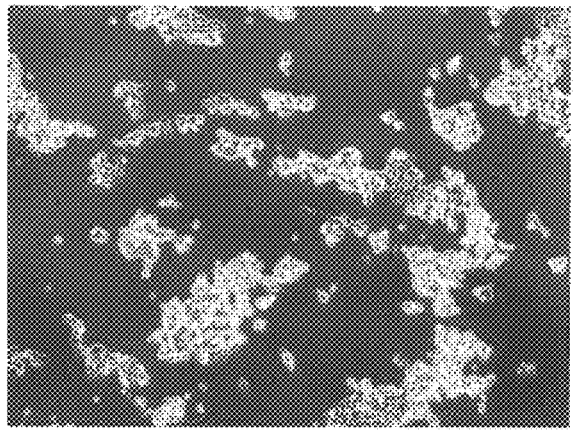
Figure 5C:
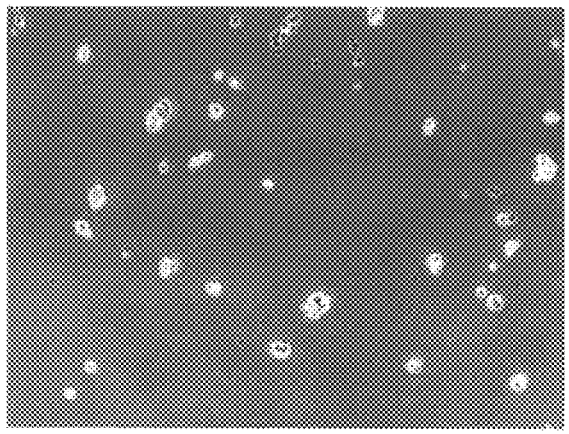
Figure 5D:
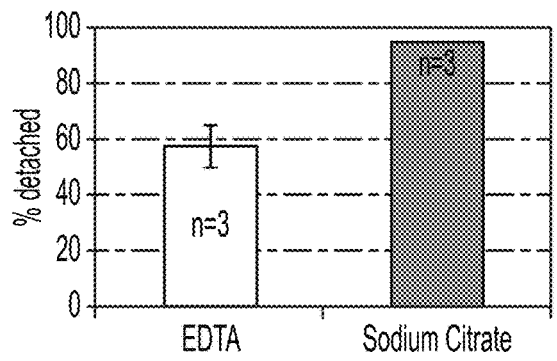
Figure 5E:
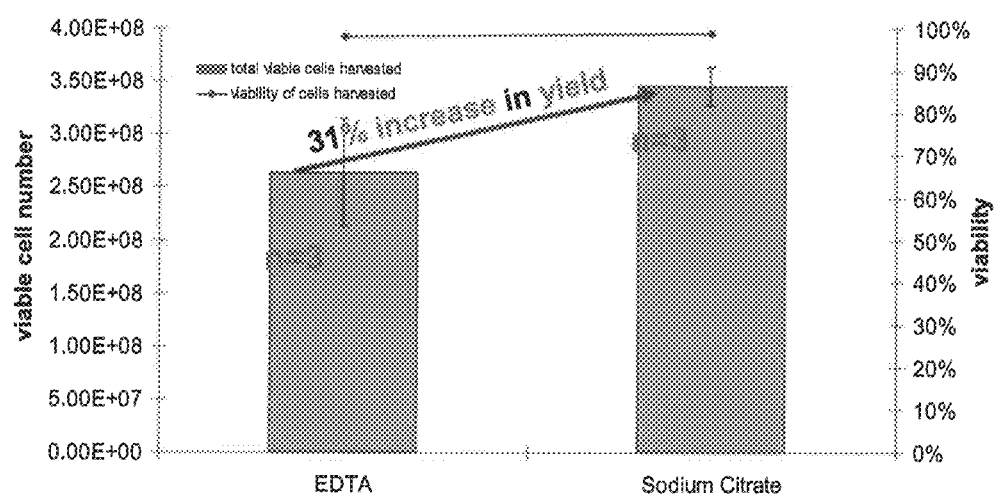

Sodium citrate formulation was tested for harvesting hESCs in two-layer cell stacks. This sodium citrate harvest was compared with the harvest using Versene® EDTA. FIGS. 5A, 5B, 5C, 5D, and 5E provides images of the cells remaining on the surface after harvest. The cultures in FIGS. 5A and 5B were both harvested using Versene® EDTA, but were handled by different operators (with the strength applied to tapping of stacks to dislodge cells varying between the operators). The operator with stronger tapping harvested ~70% of the entire culture, while the operator with weaker tapping only harvested ~45% of the culture. However, both the operators harvested more than 90% of the entire culture from the surface when sodium citrate formulation was used for the harvest (FIG. 5C). The percentage of the culture detached from each two-layer stack is plotted in FIG. 5D. The number of cells harvested from each vessel was counted and the viability of the harvest was calculated (FIG. 5E). Compared with Versene® EDTA, the counts of the cells harvested with 1× sodium citrate solution have much tighter distribution (2.64E8±5.1E7 with Versene® EDTA vs. 3.46E8±1.81E7 with sodium citrate, (see FIG. 5E), which contributes to a more robust and consistent manufacturing process. The yield of sodium citrate formulation-harvested hESC culture was 31% higher than that of Versene® EDTA harvested culture. There was less operator-to-operator variance when sodium citrate formulation was used. This may be because sodium citrate formulation disrupts the cell-surface bond more than Versene® EDTA and much less tapping effort was needed to dislodge the cells.

Additional studies to further optimize the formulation and method were conducted. In one embodiment, the optimal range for the concentration of sodium citrate for hESC detachment was 0.1×-3× (see Table 2 for the concentrations of sodium citrate and KCl), or higher. Surprisingly, sodium citrate formulations at higher sodium citrate concentrations did not necessarily detach the cells faster or break the colonies up into single cells more than lower concentrations (FIG. 6b). In fact, when working on hESCs grown in MEF-CM, sodium citrate at higher concentration (1×-3× and higher) tended to lift the hESC colonies up as whole sheets. The size of the detached hESC clump was dependent on the dilution of sodium citrate formulation more than treatment time (1-11 minutes tested). This adds to the advantage of sodium citrate formulation over Versene® EDTA, which breaks the hESC colonies into undesirable single cells at extended treatment (>9 minutes). The clump size of the detached hESC grown in mTeSR1® was overall smaller than that grown in MEF-CM. The effect of cell-detachment formulation on the size of detached clusters (clumps) of hESCs was further investigated. As described below, the osmolarity of the formulation affects the size of the clusters. In certain embodiments, a clump size of 10-1000 μm is preferred. In alternative embodiments, a clump size of 40-500 μm is desired. The operational time window for sodium citrate formulation treatment on hESCs was wider than Versene® EDTA treatment on hESCs, which is particularly beneficial in cGMP-compliant production when product quality consistency is regulated and deviation is to be minimized. The operational time window is further described below.

In exemplary experimentation presented herein, the solution included: sodium citrate and KCl diluted in $Ca^{2+}/Mg^{2+}$-free DPBS. It is, however, reasonably contemplated that alternative calcium chelators at optimized concentrations in formulations with optimal osmolarity will provide attractive results. Similarly, citrate formulations containing a salt other than KCl are contemplated. Such salts include, for example, NaCl, $Na_2HPO_3$, $NaH_2PO_3$, $K_2HPO_3$, $KH_2PO_3$, and the like.

In one embodiment, sodium citrate concentration has a preferred working range of 0.15-150 mM. In one embodiment for harvesting cells grown in culture medium such as MEF-CM (Murine Embryonic Fibroblast-Conditioned Medium), sodium citrate concentration has a working range of 1.0-50 mM. In an alternative embodiment, as illustrated in FIG. 6, sodium citrate concentration has a working range of 1.5-45 mM. In one embodiment, sodium citrate concentration for passaging cells grown in MEF-CM is a working range of 1.5-15 mM. In one embodiment, sodium citrate concentration for harvesting cells grown in culture medium such as mTeSR1® is a working range of 1.5-30 mM. Excipients in the formulation include, but are not limited to, $Ca^{2-}/Mg^{2+}$-free DPBS and KCl (1.35-1350 mM). The working osmolarity of this formulation is from 31.1-2050 mOsmol/L. In one embodiment, the working range is 290-1015 mOsmol/L. In another embodiment, the working range is 299-781 mOsmol/L. In yet another embodiment, the range is 548-781 mOsmol/L. In Table 2, sodium citrate solution of 10× contains 1350 mM KCl and 150 mM sodium citrate in water. A series of dilutions was made by diluting the 10× solution in DPBS (without $Ca^{2+}$ or $Mg^{2+}$).

TABLE 3

Osmolarity of Non-Enzymatic Detachment Solutions

Versene ®-Based EDTA solutions

|  | 0.1 mM EDTA | 0.55 mM EDTA | 1 mM EDTA | 3 mM EDTA | 10 mM EDTA |
|---|---|---|---|---|---|
| mOsmo | 273 | 272 | 281 | 287 | 305 |

Versene ®-Based EGTA solutions

|  | 0.1 mM EGTA | 0.55 mM EGTA | 1 mM EGTA | 3 mM EGTA | 10 mM EGTA |
|---|---|---|---|---|---|
| mOsmo | 282 | 282 | 283 | 290 | 311 |

Sodium Citrate (Diluted in DPBS)

|  | 0.1x | 0.3x | 0.7x | 1.0x | 1.3x | 2.0x | 3.0x | 10x |
|---|---|---|---|---|---|---|---|---|
| mOsmo | 311 | 352 | 432 | 499 | 587 | 741 | 1014 | >2050 |

Continuous counter-flow centrifugation technology can be used to concentrate and wash hESC harvest. As illustrated in FIG. 7, hESC (grown in MEF-CM) harvest is five times concentrated with 10% drop in viability after processing with kSep®. hESCs processed with kSep® remain as clusters and plate well with 10% drop in plating efficiency, compared with pre-kSep® fresh harvest (FIG. 9). hESCs formulated and vialed with M-1 filling machine cryopreserve efficiently in CryoStor10 with more than 90% viable cell recovery and 50% post-thaw plating efficiency (FIGS. 8-9).

As further discussed in Example 11, in one embodiment, the process of expanding and passaging hESCs grown in mTeSR1® from T-flasks into multilayer cell factories is optimized with a novel non-enzymatic passaging method, followed by downstream processing with continuous counter-flow centrifugation technology.

In another embodiment, hESC culture in MEF-CM is expanded, with Versene® EDTA passaging, from six-well plate into T-flasks, and further into multilayer cell culture vessels. The final harvest from multilayer cell factories was characterized with flow cytometry and more than 90% of

TABLE 2

Formulations of Sodium Citrate Solution

Dilution Factor

|  | 0.1x | 0.3x | 0.7x | 1.0x | 1.3x | 2.0x | 3.0x | 10x |
|---|---|---|---|---|---|---|---|---|
| KCl | 13.5 mM | 40.5 mM | 94.5 mM | 135 mM | 175.5 mM | 270 mM | 405 mM | 1350 mM |
| Sodium Citrate | 1.5 mM | 4.5 mM | 10.5 mM | 15 mM | 19.5 mM | 30 mM | 45 mM | 150 mM |

Osmolarity of the screened cell detachment solutions was measured (Table 3). Sodium citrate solution in general has a higher osmolarity than all the Versene®-based EDTA and EGTA solutions (solutions screened in FIGS. 2A, 2B, and 2C). This may be due to the high concentration of KCl and other excipients in the solutions. High osmolarity of the sodium citrate formulation is identified herein as one attribute that contributes to the unique cell detachment behavior of the solution, which is further discussed hereinafter. Table 3 illustrates osmolarity of various solutions.

these cells expressed pluripotency markers including OCT4, SSEA4, Tra-1-60, and Tra-1-81. The final cell harvest was concentrated more than 14 times after automated downstream processing, with only 2% drop in cell viability.

Further studies related to treatment time and its correlation with the dilutions of the citrate formulation were conducted and are further defined below in Table 4. FIGS. 10 and 11 demonstrate the effect of the dilution of sodium citrate formulation on the trend of culture harvest increase with the increase of treatment time. The study illustrated in FIG. 10 was conducted on hESC culture grown in MEF-CM, and the study illustrated in FIG. 11 was conducted on hESC culture grown in mTeSR1®.

TABLE 4

| | | in MEF-CM | in mTeSR1 ® |
|---|---|---|---|
| | | treatment time window | |
| Sodium Citrate dosage | 0.1X | | 8 min-10 min |
| | 0.3X | 4 min-11 min | 6 min-10 min |
| | 0.7X | 3 min-11 min | 4 min-10 min |
| | 1X | 3 min-11 min | 3 min-10 min |
| | 1.3X | 3 min-11 min | 2 min-10 min |
| | 2X | 3 min-11 min | 3 min-10 min |
| | 3X | 5 min-11 min | |
| | | minimal treatment time (min) to achieve 85% detachment | |
| Sodium Citrate dosage | 0.1X | | 8 |
| | 0.3X | 4 | 6 |
| | 0.7X | 3 | 4 |
| | 1X | 3 | 3 |
| | 1.3X | 3 | 2 |
| | 2X | 3 | 3 |
| | 3X | 5 | |

It is contemplated that with the sodium citrate formulations the cells can be harvested from a variety of surfaces including but not limited to Matrigel-coated surface, gelatin-coated and MEF-plated surface, and/or chemically defined surfaces. Examples include, for example, synthetic plastic or peptide-bound surfaces (Corning Synthemax and Nunclon (Nunc) Vita surfaces), surfaces coated with defined recombinant or native proteins (e.g. vitronectin, fibronectin, laminin and collagen). There are two widely-used surfaces for hPSCs: the MEF-seeded surface (Murine Embryonic Fibroblasts are seeded onto surface pre-coated with gelatin), and Matrigel-coated surface (Matrigel is an extracellular matrix derived from mouse tumor). Both Synthemax and Nunc Vita are defined surfaces available on the market and marketed as a surface that can be used for hPSC culture. Sodium citrate formulations can be used to harvest hPSCs grown in various types of culture medium, including, but not limited to, regular culture medium used for culturing hPSCs on MEF-seeded surfaces, MEF-CM, mTeSR1® and StemPro®.

Example 2 (All the Studies in Example 2 were Conducted on hESC Cultures in mTeSR1®)

Determination of Optimum Sodium Citrate Formulation
Comparative Effects of Osmolarity, Potassium, and Sodium on the Ability of Sodium Citrate to Promote Cell Detachment The 1× sodium citrate formulation described above is 15 mM sodium citrate, 135 mM KCl, pH 7.31, and 499 mOsmol/L in DPBS. Further studies were performed to determine the effects of osmolarity, KCl on the ability of the sodium citrate formulation to promote cell detachment. FIG. 12 shows the percentage of detachment of hESC in cultures treated with various solutions of sodium citrate. The results indicate that the osmolarity of the solution and the concentration of sodium citrate are important factors for achieving optimal cell detachment. In addition, at nearly normal osmolarity, the addition of potassium (KCl) to the sodium citrate formulation caused greater percentage detachment than the addition of sodium (NaCl) (compare solution #4 to solution #5) suggesting that KCl may be a better choice of salt in this formulation than NaCl. Not to be limited by theory, one possible explanation for this finding is that the additional sodium ($Na^r$) inhibits the electrolysis of sodium citrate and consequently lowered the availability of the $Ca^{2+}$ chelating citrate ions.

Effect of Osmolarity on the Ability of Sodium Citrate to Promote Cell Detachment and Maintain Viability Studies were performed to determine the effect of osmolarity on the ability of sodium citrate to promote hESC detachment. Sodium citrate solutions/formulations of various osmolarity were prepared by adjusting the concentration of KCl and maintaining a constant concentration of sodium citrate (see FIG. 13). As shown in FIG. 14A, high (and approximately the same) viability was observed with all solutions whereas maximum harvesting of cells was achieved after treatment of cells for 5 minutes with sodium citrate solutions (15 mM citrate) having an osmolarity of between 299-781 mOsmol/L. Substantially reduced harvesting was observed using a sodium citrate solution with an osmolarity of 169 mOsmol/L and an osmolarity of 1016 mOsmol/L suggesting that there is a threshold between about 299-781 mOsmol/L at which high percentage of culture could be harvested. In fact, microscopic images (FIG. 14B) revealed substantially larger clusters of harvested cells from cultures treated with 781-1016 versus 169-548 mOsmol/L solutions of sodium citrate. The images of the detached clusters were analyzed and the sizes of the clusters were quantified. The distribution of the cluster sizes is shown in FIG. 14C. As demonstrated in images and the size distribution plot. The percentage of the culture harvested as large cell clusters was increasing with the increase of the osmolarity. There was a substantial increase in the measured sizes of the detached clusters obtained from cultures treated with 781-1016 mOsmol/L solutions versus 169-548 mOsmol/L solutions (mostly 250-900 equidiameter size clusters versus mostly 40-150 equidiameter size clusters, respectively).

Effect of Sodium Citrate Concentration on Cell Detachment and Viability

Studies were performed to determine the effect of citrate concentration on hESC detachment and viability. Sodium citrate solutions of various concentrations were prepared at about 265 mOsmol/L and a pH of about 7.2. As shown in FIG. 15A, high (and approximately the same) viability was observed with all solutions whereas the percentage of harvested cells increased with increasing concentrations of up to about 30-45 mM sodium citrate. Only slightly improved harvesting was achieved using 75 mM sodium citrate. However, there appeared to be a threshold between about 30-75 mM sodium citrate at which "sheeting harvest" (hESC colonies detached as big clusters or sheets of cells) occurred. In fact, microscopic images revealed substantially larger clusters of harvested cells from cultures treated with 30-75 mM sodium citrate solutions of sodium citrate (FIG. 15B). There was a corresponding increase in the measured sizes of clusters obtained from cultures treated with 30-75 mM sodium citrate solutions versus 1.5-15 mM sodium citrate solutions (mostly 250-900 equidiameter size clusters versus mostly 40-150 equidiameter size clusters, respectively) (FIG. 15C).

Comparative Effects of EDTA, EGTA, and Sodium Citrate on Cell Detachment

Studies were performed to determine the comparative effects of chelators on hESC detachment. The $Ca^{2+}$ chelation capacity of citrate, EDTA, and EGTA are 1:1.5, 1:1, and 1:1, respectively, based on stoichiometry. EDTA also binds $Mg^{2+}$ and other metals whereas EGTA is more specific for binding of $Ca^{2-}$. Cell detachment achieved by a solution of sodium citrate (15 mM sodium citrate at 400 mOsmol/L (achieved by addition of KCl) and a pH of 7.8) was compared to that achieved by 22.5 mM and 45 mM solutions of EDTA and EGTA at 400 mOsmol/L and a pH of 7.8. As shown in FIG. 16A, EDTA and EGTA at concentrations higher than 22.5 mM detached hESC colonies as effectively as sodium citrate. The measured sizes of redistributed clusters obtained from cultures treated with the various solutions were similar (mostly 40-200 equidiameter size clusters) (FIG. 16B).

Example 3

Time Course Studies
Versene® EDTA Versus Sodium Citrate

Studies were performed to determine the operational time windows that provide good percentage detachment and cluster size distribution. The detachments in the studies described above were evaluated after five minute treatment with cell detachment formulations. Here, treatment time is extended up to 20 minutes, and detachment and cluster size are examined under various time points (2, 5, 8, 10, 15 and 20 minutes). Formulations of moderate osmolarity and pH are selected from prior studies and the time span (operational window) of treating hESC culture with these formulations that would yield a desirable percentage detachment and post-detachment cluster size distribution is determined. Cell cultures were treated with the solutions of FIG. 17 for 2, 5, 8, 10, 15 or 20 minutes and then tapped twice to dislodge the cells. For each treatment time point, cultures were evaluated for percentage detachment of cells and cluster size in order to determine the optimal operational window. Cell viability and plating efficiency of detached cells were evaluated at the 5, 10, and 20 minute time points. FIG. 18A shows the effects of Versene EDTA and various sodium citrate solutions on hESC percent detachment at each treatment time point. FIGS. 18B-1, and 18B-2 shows the effects of Versene® EDTA and various sodium citrate solutions on cluster size distribution at each treatment time point. FIG. 19 shows the effects of Versene® EDTA and various sodium citrate solutions on the plating efficiency of detached cells at each treatment time points of 5, 10 and 20 minutes.

Based on the results obtained from this study, and not to be limited by theory, an operational window similar to that depicted in FIG. 20A can be established and appropriate parameters can be selected to achieve a desired percentage of cell detachment and cluster size (equi-diameter). For example, as shown in FIG. 20B the criteria used to determine the operational window is (1) the percentage of culture detached is over 70% and (2) the percentage of culture detached as 40-500 um clusters is over 90%. As indicated by the experiment data, in general, the percent detachment increase with the increase of the treatment time and the cluster size decrease with the increase of the treatment time. Based on these plots, treating hESC culture with citrate formulation Dis2#3 for 3.5 to 7 min (operational window) would result in detaching >70% of the culture as mostly (>90%) 40-500 um clusters. The operational windows determined under the same criteria for other citrate formulations and Versene® EDTA are narrower. In fact, based on the plot, to meet the same criteria with Versene® EDTA, the culture needs to be treated for exactly 10 min (0 duration). Wider operational window, which gives more operational flexibility without affecting the consistence of product characteristics, is more desirable, especially in cGMP production. Based on FIG. 19, plating efficiency drops with the increase of the treatment time and longer than 10 min treatment time is not desirable because of this. Accordingly, best practice (based on high percent detachment, desirable cluster size range and high plating efficiency) for detaching hESCs with citrate formulation Dis2#3 would be 5-7 min treatment, and 10 min treatment with Versene® EDTA. At their respective optimal treatment times, Versene® EDTA harvested over 20% fewer cells than sodium citrate.

High Concentration of EDTA and EGTA

Following the same basic approach as used above for determining the operational windows for various sodium citrate formulations and Versene® EDTA, experiments were performed to determine the operational windows and plating efficiency for 22.5 mM Versene® EDTA and 22.5 mM EGTA formulations described in Example 2, as comparison to Versene® EDTA and sodium citrate (formulation Dis2#3). The operational windows were determined based on the criteria of ">70% of the culture is harvested and >90% of the cells harvested are in the format of 40-500 µm cluster". As shown in FIG. 21A, the durations of the operational windows of 22.5 mM EGTA and Versene® EDTA formulations are similar to that of citrate formulation Dis2#3, and are much wider than that of Versene® EDTA. The starting time points of the operational windows of 22.5 mM EGTA and EDTA formulations are the same, and are earlier than that of citrate formulation Dis2#3. However, as shown in FIG. 21B, hESCs detached with 22.5 mM EGTA and EDTA formulations did not re-plate well (5, 15 and 20 min treatment time points examined), and sodium citrate (solution Dis2#3) substantially outperformed high-concentration (22.5 mM) EDTA and EGTA formulations in terms of cell plating efficiency post-harvest (plotted are plating efficiencies at 5 minute treatment time point normalized with that of citrate formulation Dis2#3).

It is demonstrated herein that sodium citrate formulations outperform EDTA-containing and EGTA-containing formulations in passaging hPSCs. Furthermore, another advantage of sodium citrate over EDTA and EGTA is that leftover sodium citrate should have less deleterious effects on cell cultures than EDTA or EGTA. (Sodium citrate is sometimes used as a normal component in various culture media of various cell types.) For example, as seen in Example 6, sodium citrate formulation solutions do not necessarily need to be removed after treating the cells.

However, additional passaging and harvesting formulations are contemplated herein including formulations containing EDTA and EGTA, other $Ca^{2+}$ chelators besides sodium citrate, or combinations of various $Ca^{2+}$ chelators. Two factors are identified related to cell detachment, the $Ca^{2+}$ chelator concentration and osmolarity. When the concentration is too low, the bond between the cells and the matrix is not effectively disrupted and the formulation cannot effectively detach the cells. When the concentration is too high, the bond between the cells is overly disrupted, the size of the detached clusters decrease, and the detached clusters can be fragile and easily disintegrated when further handled.

Not to be limited by theory, the shrinking of the cells or the colonies caused by high osmorality can result in cell detachment, especially at the edge of the colonies. However, the cells could also be damaged if the osmolarity is too high. As illustrated herein, when the osmolarity is too high, the cells are not effectively detached from the surface. Example 4, provides studies toward further optimization. Through use of the experimental design disclosed herein, other cell-detaching/passaging formulations containing various $Ca^{2+}$ chelators can be developed and are considered within the scope of the present invention.

Example 4

Optimization of Sodium Citrate Formulations Towards High Plating Efficiency After Extended Treatment Studies were performed to determine the optimum sodium citrate formulation to be used for achieving high plating efficiency of the hESC clusters detached after extended treatment with sodium citrate solution. hESC culture was treated with solutions of varying sodium citrate concentration (1, 5, and 10 mM) and osmolarity (400, 500, 600, 700, and 800 mOsmol/L, achieved by adjusting the concentration of KCl) for 5, 10, 15, and 20 minutes. At the indicated treatment time points, percent harvest, cluster size, and re-plating efficiency were compared for each sodium citrate solution. To quantify re-plating efficiency, $2 \times 10^5$ viable cells detached from the surface were re-plated onto one well of a six-well plate coated with Matrigel, and the attached cells were harvested and counted the next day. Assuming that the re-attached cells grew to double their population within one day, the re-plating efficiency was then calculated as the number of the cells harvested the next day divided by $4 \times 10^5$. As shown in FIGS. 28A-1, 28A-2. 28A-3, 28A-4, 28A-5: 1/ cluster size decreases with the increase of the treatment time; 2/ cluster size decreases with the increase of sodium citrate concentration; and 3/ cluster size increases with the increase of the osmolarity. Results indicated that compared with all solutions tested, the low sodium citrate concentration solution (1 mM) with high osmolarity (600-700 mOsmol/L) produced good cell detachment, large clusters and high plating efficiency even after extended treatment (FIGS. 28A-1, 28A-2. 28A-3, 28A-4, 28A-5, 28B and 28C). However, high osmolarity (>700 mOsmol/L) appeared to cause hESC cluster roll-up at detachment, which can result in undesired morphology of the re-plated colonies and cell death or differentiation at the centers of those colonies.

Example 5

Use of Sodium Citrate in Dry Passaging

Loss of the cells can occur during treatment with cell-detaching solutions. This is because the culture is soaked in the solution during treatment, and the solution is removed prior to detaching the culture with cell culture medium. In order to eliminate this loss, studies were performed to find out whether the solution can be added and removed right away at the beginning of the treatment, and whether the culture can be detached with only the residue of the solution on the culture surface ("dry passaging"). The proposed new procedure is depicted in FIG. 22. As also indicated in FIG. 22, two treatment time points (5, 10 min), two incubation conditions (Room Temperature, 37° C. incubator) were compared, and both Versene® EDTA and citrate formulation Dis2#3 were tested for this dry passaging procedure. Based on the cluster size distributions and the images of re-plated cells, it was determined that "dry passaging" procedure works for both Versene® EDTA and citrate formulation, and the best condition based on this experiment was 5 min of incubation at room temperature. "Dry passaging" could be adopted to avoid the harvest loss in detachment solutions. Although additional optimization of the citrate formulation for the application in "dry passaging" to yield high detachment, desirable cluster size distribution and re-plating efficiency can be determine by one of ordinary skill in the art, one exemplary formulation is Dis2#3.

Example 6

Use of Sodium Citrate in Leave-In Passaging

As another alternative approach to streamline the detachment and passaging procedure and to avoid the loss of cells at the removal of the cell-detaching solutions, "leave-in passaging" procedure was evaluated. FIG. 24 depicts the methodology used in "leave-in passaging". Basically, after soaking the culture with the cell-detaching solution for a certain treatment time, the solution is not removed from the culture; instead, it is left in the culture and neutralized with culture medium. The cells are then dislodged from the surface by a swirling motion, and seeded onto a fresh surface afterwards. The cell-detaching solution is left in the final cell harvest and is later transferred into the next passage of the culture when the cell harvest is seeded onto fresh surface. Given that citrate is sometimes used as a normal component of some cell culture medium, the remaining citrate should not have deleterious effects on cell cultures. Such a protocol provides increased ease-of-use and scalability of the sodium citrate formulations for cell detachment. For example, the solutions are not required to be removed from the culture vessel and tapping of the vessel is not used to dislodge the cells. The protocol could be applied in small scale bench-top culture plate culture format; it could also be applied in, for example, harvesting cells grown in 10-layer, or even 40-layer cell culture vessels that have to be handled by robots (e.g. Automatic Cell Factory Manipulator).

The study described in FIG. 24 was conducted on hESC culture grown in StemPro® medium. The culture was treated with two sodium citrate formulations, solution #3 and #13 described in Example 4, at the volume of 0.5 mL and 0.75 mL. FIG. 25 shows the post-detachment viable cell number and percent viability achieved using leave-in passaging with the two sodium citrate formulations. FIG. 26 shows the post-detachment cluster size distribution and plating efficiency achieved using leave-in passaging with the two sodium citrate formulations. The data indicate that both sodium citrate formulations worked well and provided comparable results; complete detachment occurred within 7-10 minutes, cell viability post-detachment was >95%, clusters were primarily large (20-75% post-detachment cells were in the format of clusters of >200 µm equidiameter; <8% were <40 µm), and the post-detachment plating efficiency was as high as around 80%. In addition, the data also indicate that 0.5 mL of cell-detachment citrate solution was sufficient to detach the cells, and the size of post-detachment hESC clusters were relatively smaller when 0.75 mL solution was used.

Example 7

Passaging of Mesenchymal Stem Cells

Studies were performed to assess the effect of sodium citrate formulations, which were optimized for hESC detachment, on detaching and passaging MSCs. Four formulations were used and compared: Versene® EDTA, citrate Dis2#3, citrate #3 and citrate #13 (indicated as citrate 2-3, 3 and 13 in FIG. 27). As shown in FIG. 27, sodium citrate solution #3 provided optimum results. Treatment of MSCs with citrate #13 for 10 minutes followed by tapping of the vessel was sufficient to detach 80% of the cells, and resulted in 90% post-detachment viability and the best post-detachment replating, compared with the other three formulations.

Example 8

Evaluation of Sodium Citrate Formulations as Cell Detachment and Passaging Solutions in Long-Term Cultivation of hESCs The citrate formulations described above were initially identified and optimized for applications in harvesting and passaging hESCs grown in large-scale in closed culture vessels. To dislodge the cells after the treatment with the cell-detaching solutions, culture vessels were agitated by tapping, swirling or shaking in the experiments to simulate the cell detachment process in closed culture vessels. In small scale bench-top cultivation of hPSCs, open culture platforms, e.g. six-well plates or T-flasks, are often used, and cells are accessible to be dislodged by hosing with a stream of culture medium, as described in Table 1 under "EDTA method". To evaluate the use of sodium citrate solutions in the small-scale bench-top applications, a preliminary study was conducted to test citrate solution #3 and #13 on hESC culture in six-well plate, and compared their performance with Versene® EDTA. The culture was grown in mTeSR1® medium and was treated for 5-8 minutes with the formulations followed by hosing (note that for large scale application, longer treatment, around 10 min, may needed). Treatment of hESC cultures with either solution for 5 minutes followed by hosing with a pipette works well and achieves 95% harvesting and approximately 70-85% replating efficiency. The replating efficiency of citrate solution #13 was about 15% higher than that of Versene® EDTA.

Long term hESCs cultures in StemPro® and mTeSR1® were initiated and maintained for over 50 passages (about 8 months) by continuously passaging with citrate formulations. Sodium citrate solutions Dis2#3, #3 and #13 were evaluated and Versene® EDTA was included in this study as a comparison to the citrate formulations. As shown in FIG. 29, hESCs passaged with citrate solution #13 for 31 passages in StemPro® medium, and 34 passages in mTeSR1®, respectively, stained positive for hESC markers, including OCT4, Sox2, Nanog, SSEA4, TRA-1-60 and TRA-1-81). The marker expressions were further quantified with flow cytometry. 80-100% of the hESCs passaged with the citrate solution for 36 passages in StemPro®, and 30 passages in mTeSR1®, respectively, stained positive for OCT4, SSEA4, TRA-1-60 and TRA-1-81, and the percentages of positive cells were comparable to those of cells directly thawed out from the hESC bank (the starting cells for the long term culture). The characterization results from both immunocytochemistry and flow cytometry shows that long-term passaging with sodium citrate formulation supports sustainable culture, or self-renewal of hESCs.

Pluripotency of these hESCs was further evaluated for differentiation capability. As shown in FIG. 30, hESCs passaged with citrate solution for 40 passages in StemPro® and 35 passages in mTeSR1®, respectively, were capable of generating embryoid bodies (EBs) and differentiating into all three germ layers, endoderm, mesoderm and ectoderm. The differentiation capability of the long-term hESC culture in StemPro® was further confirmed by the generation of teratomas of these cells in immunodeficient SCID mice (FIG. 31). The results from EB differentiation and teratoma generation proved that hESCs passaged with citrate solution for numerous passages and prolonged time are still pluripotent and retain the capability of differentiating into all kinds of somatic cells.

G-banding karyotype of the long term hESC culture passaged with citrate solution was examined for abnormality. Three samples of hESCs cultured in StemPro® medium were karyotyped normal after passaged for 10 and 25 passages with the citrate solution #13; in contrast, whereas three samples of hESCs are normal after 10 passages with Versene® EDTA, one out of three samples are abnormal and one sample had emerging abnormality after 25 passages with Versene® EDTA. HESCs cultured in mTeSR1® medium were also karyotyped normal after passaged for 29 times with the citrate solution #13.

The split ratio used to passage the long term hESC cultures was 1:15 to 1:40 (i.e. for example, cells harvested from one well could be split into 15 to 40 fresh wells; in the context of hPSC cultivation, 1:40 is considered higher split ratio than 1:15), in both mTeSR1® and StemPro®. The cultures typically reached confluence on day 4 or day 5 after split. In traditional hPSC cultivation, where enzymatic treatment and scraping is used to passage the cells, the split ratio is typically 1:2 to 1:6, and the culture typically reaches confluence between day 5 and day 7. Compared with the traditional passaging method, the passaging method disclosed herein results in much faster expansion of the culture. This not only benefits manufacturing cells in large scale, but also shortens the waiting time between experiments in bench-top studies. One concern related to high split ratio and fast expansion is the emergence of abnormal karyotypes. However, as described above, the cultures in both mTeSR1® and StemPro® maintained normal karyotype after extended cultivation using sodium citrate formulation as passaging solution.

Example 9

Determination of Operational Window for Selected Sodium Citrate Formulation

The time course study described in Example 3 was conducted to determine the operational windows for citrate solution #13. Versene® EDTA was used as a control in this study. The experiment method was slightly modified from the study in Example 3; the percent harvest was quantified based on cell counts instead of visual assessment. As compared with Versene® EDTA, sodium citrate solution #13 harvested more cells in shorter treatment time. There was bigger population of cells in the ">200 um" category when citrate solution was used, according to the "Cluster Size" plot. As a result, citrate solution #13 had a wider operational window (8-11.5 min) than Versene® EDTA. In fact, the "Operational Window" of Versene presented no overlap in time frame to satisfy both requirements ("% harvest" >70%, and "clusters bigger than 40 um" >90%). The cells detached with citrate #13 had comparable plating efficiency with those detached with Versene® EDTA (data not shown). Overall, sodium citrate solution #13 outperforms Versene® EDTA

Example 10

Detaching and Passaging Human Induced Pluripotent Stem Cells (iPSCs) and Multiple Lines of Human Embryonic Stem Cells with Sodium Citrate Formulations In this Example 10, sodium citrate formulations were tested on other hESC lines (in addition to H9) and human iPSCs. Sodium citrate solution #13 was used to passage H7 and H14 hESCs grown in mTeSR1®. Unlike the H9 cultures used in the other studies, the starting cultures of H7 and H14 had many stroma or differentiated cells. The citrate solution selectively detached and passaged mostly the undifferentiated hESCs, and left the stroma and differentiated cells on the surface. Following three consecutive passages with the solution, the morphology of both the H7 and H14 cultures was greatly improved with no obvious stroma or differentiated cells observed. It follows that the sodium citrate formulations can be used to detach and passage various hESC lines.

Citrate solution #13 can be used to detach and passage iPSCs. Even when the cells were transferred from MEF feeders onto Matrigel, the attachment was good when the detached cells were re-plated, and the majority of the MEF feeders was not detached and hence not subsequently transferred onto the fresh Matrigel surface. In this experiment, the human iPSC culture was also gradually adapted into defined medium (StemPro®) in five days at passage 1. It therefore follows that the citrate formulations can be applied onto various human iPSC lines for passaging and maintaining the established culture. The formulation can further be used to transfer the hPSC cells, including hESCs and human iPSCs, from MEF feeders onto feeder-free surfaces, like Matrigel, with reduced time to clear up the remaining MEFs (compared with mechanical passaging methods involving scraping). Application of citrate formulations in the initial phase of human iPSC generation can help speed up the process of establishing the culture in feeder-free and/or defined conditions.

Example 11

Large-Scale Culture and Downstream Processing of hESCs Using Sodium Citrate Solutions The study described in Example 1 where hESCs were harvested from two-layer cell culture vessels (e.g. Corning Cell Stacks) using a sodium citrate formulation was conducted on cells cultured in MEF-CM, and the formulation was composed of 15 mM sodium citrate, 135 mM KCl in DPBS. The current example describes the study in which citrate solution #13 was used to harvest hESCs grown in mTeSR1®. Prior to scaling up the culture from six-well plate into multi-layer cell factories, citrate solutions #3 and #13 were assessed and compared with Versene® EDTA in detaching hESC from larger culture vessels, i.e. T225 flasks instead of 6-well plates. Two hESC lines, H9 and H14 were used. The cultures were treated with citrate solutions for 10 minutes and then incubated in culture medium for 2 minutes before the flasks were tapped to dislodge the cells. The results indicated that both solutions are good for large-scale harvesting and provide greater harvesting than Versene® EDTA (for example, 30% higher than Versene® EDTA for H9 cells and 15-20% higher than Versene® EDTA for H14 cells) with similar cluster size distributions (primarily 40-200 µm) among both solutions and Versene® EDTA for both cell lines (data not shown). In detaching H14 cells, solution #13 seemed to slightly outperform solution #3 (5% more harvest, and bigger clusters with #13). Therefore, citrate solution #13 was used in the study of scaling up hESC cultures into multi-layer cell culture vessels.

Regardless of the method used to obtain hESCs, compatible downstream processing technologies are also needed to concentrate and purify the cells in the final harvest. As mentioned previously, current therapeutic cell volume reduction and purification technique using open centrifugation technology is time consuming, introduces high process risk, and is cost prohibitive for high volume batches. After processing with KSep, the size distribution of the hESC clusters harvested by sodium citrate solution #13 did not change significantly, indicating that KSep processing was not significantly breaking up the clusters. The viability of the cells after KSep was as high as over 80%, and the plating efficiency was over 60%, only 13% lower than the plating efficiency before KSep. The images of the Day 1 re-plated cultures also indicated that the hESC clusters harvested with the citrate solution were not fully disintegrated into single cells or smaller clusters by KSep processing. Overall, sodium citrate solution #13 is capable of generating robust clusters that survive kSep®, automated vialing and cryopreservation with Controlled-Rate Freezer, retain high viability and plating efficiency, and present normal karyotype post-scaling up.

Having now described a few embodiments of the invention, it should be apparent to those skilled in the art that the foregoing is merely illustrative and not limiting, having been presented by way of example only. Numerous modifications and other embodiments are within the scope of one of ordinary skill in the art and are contemplated as falling within the scope of the invention and any equivalent thereto. It can be appreciated that variations to the present invention would be readily apparent to those skilled in the art, and the present invention is intended to include those alternatives. Further, since numerous modifications will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method for harvesting and subsequent passaging of human pluripotent stem cells "hPSCs", comprising:
    passaging the hPSCs with a preferred non-enzymatic cell detaching solution, at a split ratio of 1:10 to 1:60;
    wherein the culture reaches confluence within seven days after split;
    wherein said preferred non-enzymatic cell detaching solution is identified as follows:
        creating a plurality of non-enzymatic cell detaching solutions, each of said non-enzymatic cell detaching solutions comprising at least one Ca2+ chelator at varying concentrations, and each of said cell detaching solutions having varying osmolarity, wherein said osmolarity is between 273 mOsmol/L to 1014 mOsmol/L;
        testing each of said plurality of non-enzymatic cell detaching solutions, said testing comprising: test passaging hPSCs with each of said plurality of non-enzymatic cell detaching solutions, at a split ratio of 1:10 to 1:60 to yield test cells and determining percentage of culture detached at a given treatment time and determining average cluster size of said test cells; and
        selecting said preferred non-enzymatic cell detaching solution from said plurality of cell detaching solutions, wherein said selection is based upon desired percentage of culture detached at a given treatment time and desired average cluster size;
    wherein said selected preferred non-enzymatic cell detaching solution is used for said passaging step.

2. The method of claim 1, wherein said passaging occurs in cell culture plates or vessels.

3. The method of claim 1, wherein the average cluster size is about 40-500 µm.

4. The method of claim 1, further comprising:
    downstream processing of clusters, wherein downstream processing is selected from the group consisting of continuous counter-flow centrifugation technology, formulation, automated vialing and cryopreservation.

5. The method of claim 1, wherein the hPSCs maintain pluripotency and normal G-banding karyotype at over 50 passages.

6. The method of claim 1, wherein the split ratio is 1:15 to 1:40.

7. The method of claim 1, wherein the osmolarity is 250-1050 mOsmol/Liter.

8. The method of claim 1, wherein the osmolarity is 311-1014 mOsmol/Liter.

9. The method of claim 2, wherein the cell culture plates or vessels are selected from the group consisting of petri dishes, multi-well cell culture plates, stacked cell culture apparatus, and cell culture factories.

* * * * *